US007547794B2

(12) United States Patent
Green et al.

(10) Patent No.: US 7,547,794 B2
(45) Date of Patent: Jun. 16, 2009

(54) COMPOSITIONS USEFUL AS INHIBITORS OF PROTEIN KINASES

(75) Inventors: Jeremy Green, Burlington, MA (US); Alex Aronov, Watertown, MA (US); Albert C. Pierce, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 814 days.

(21) Appl. No.: 10/808,678

(22) Filed: Mar. 25, 2004

(65) Prior Publication Data

US 2004/0198750 A1 Oct. 7, 2004

Related U.S. Application Data

(60) Provisional application No. 60/460,042, filed on Apr. 3, 2003.

(51) Int. Cl.
*C07D 311/00* (2006.01)
(52) U.S. Cl. .................. 549/399; 549/404; 549/408
(58) Field of Classification Search ............ 514/254.11, 514/233.5, 456, 365, 403, 406, 337, 320, 514/397; 546/114; 549/403, 404, 399, 408; 544/279
See application file for complete search history.

(56) References Cited

U.S. PATENT DOCUMENTS 4,065,574 A * 12/1977 Moon et al. ................. 514/456
5,593,989 A * 1/1997 Peglion et al. ........... 514/229.5
5,733,920 A 3/1998 Mansuri et al.

FOREIGN PATENT DOCUMENTS

WO WO 98/17662 4/1998
WO WO 01/53266 7/2001

OTHER PUBLICATIONS

Dermer (Bio/Technology, 1994, 12:320).*
Freshney (Culture of Animal Cells, A Manual of Basic Technique, Alan R. Liss, Inc., 1983, New York, p. 4).*
MSNBC News Services, "Mixed results on new cancer drug", Nov. 9, 2000.*
Gura (Science, v278, 1997, pp. 1041-1042).*
(Gulati et al. STN Accession No. 1936:61866; Document No. 30:61866; Abstract of Current Science (1936),5,75).*
Ishchenko et al. STN: Accession # Abstract of Geterotsiklicheskikh Soedinenii) (2002), 38(3), 274-280.*
Lacova et al. STN Accession # Abstract of Molecules [Electronic Publication] (1998), 3(3), 120-131.*
Meshcheryakova et al. STN Accession # Abstract of Khimiko-Farmatsevticheskii Zhurnal (1976), 10(3), 37-41.*
Basinski et al STN Accession # Abstract of Polish Journal of Chemistry (1991), 65(9-10), 1619-32.*
Ishchenko et al. STN Accession # Abstract of Khimiya Geterotsiklicheskikh Soedinenii (1995), (3), 322-4.*
Grishko et al. Ukrainskii Khimicheskii Zhurnal (Russian Edition) (1985), 51(2), 211-17.*
Balbi et al. STN Accession # Abstract of Farmaco, Edizione Scientifica (1982), 37(6), 387-97.*
Beugelmans et al. STN Accession # Abstract of Tetrahedron Letters (1976), (25), 2145-8.*
Vorozhtsov et al STN Accession # Abstract of Doklady Akademii Nauk SSSR (1965), 164(5), 1046-9.*
Bell et al. STN Accession # Abstract of Australian Journal of Chemistry (1963), 16(4), 690-4.*
Blicke et al. STN Accession # Abstract of Journal of Organic Chemistry (1960), 25, 693-8.*
Beugelmans et al. STN Accession # Abstract of Tetrahedron Letters, 1976 25, 2145-8.*
Aitmambetov et. al. STN Accession # Abstract of (Natural Compounds (Translation of Khimiya Prirodnykh Soedinenii) (2000), 36(1), 47-50).*
Ishchenko et al. STN Abstract of Geterotsiklicheskikh Soedinenii) (2002), 38(3),274-280.*
Murti et al., STN Abstract of Tetrahedron Letters (1964), (39-40), 2995-7.*
Kariyone STN Abstract of Yakugaku Zasshi (1960), 80, 746-9; Yakugaku Zasshi (1960), 80, 749-52.*
Spatz, STN Abstract of Journal of Organic Chemistry (1959), 24, 1381-2.*
Rahatgaonkar et al. STN Abstract of Indian Journal of Heterocyclic Chemistry (1996), 5(4), 323-324.*
Basinski et al. STN Abstract of Polish Journal of Chemistry (1991), 65(9-10), 1619-32.*
Kostanecki et al. STN Abstract of Berichte der Deutschen Chemischen Gesellschaft (1908) 41, 783-6.*
Basinski, STN Accession No. 1992:214399 Document No. 116:214399; Abstract of Polish Journal of Chemistry (1991), 65(9-10), 1619-32.*
Heideman et al., "Suppression of tumor growth, invasion and angiogenesis of human gastric cancer by adenovirus-mediated expression of $NK_4$," *J. Gene Medicine* 6: 317-327 (2004).
Tomioka et al., "Inhibition of growth, invasion, and metastasis of human pancreatic carcinoma cells by NK4 in an orthotopic mouse model," *Cancer Research* 61: 7518-7524 (2001).
Saga et al., "Expression of HGF/NK4 in ovarian cancer cells suppresses intraperitoneal dissemination and extends host survival," *Gene Therapy* 8: 1450-1455 (2001).
Martin et al., "Growth and angiogenesis of human breast cancer in a nude mouse tumour model is reduced by NK4, a HGF/SF antagonist," *Carcinogenesis* 24(8): 1317-1323 (2003).
Davies et al., "The HGF/SF antagonist NK4 reverses fibroblast- and HGF-induced prostate tumor growth and angiogenesis in vivo," *Int. J. Cancer* 106:348-354 (2003).

(Continued)

*Primary Examiner*—D. Margaret Seaman
*Assistant Examiner*—Nizal S Chandrakumar
(74) *Attorney, Agent, or Firm*—Daniel A. Pearson

(57) ABSTRACT

The present invention relates to compounds useful as inhibitors of protein kinases. The invention also provides pharmaceutically acceptable compositions comprising said compounds and methods of using the compositions in the treatment of various disease, conditions, or disorders.

17 Claims, No Drawings

OTHER PUBLICATIONS

Christensen et al., "A selective small molecule inhibitor of c-Met kinase inhibits c-Met-dependent phenotypes in vitro and exhibits cytoreductive antitumor activity in vivo," *Cancer Research* 63: 7345-7355 (2003).

Edwards et al., "Antineoplastic Activity and Cytotoxicity of Flavones, Isoflavones, and Flavanones", Abstract XP-009035912, J. of Natural Products, pp. 85-91, 1979.

Database Chemabs, "Amino Acid Derivatives and Oximes of Flavones" Abstract XP-002295239, Chem. Of Heterocyclic Compounds, 2002.

Database Chemabs, "Benzo-.gamma.-pyrones. Part XIV. Reaction of C-substituted 2-phenyl-4H-1-benzopyran-4-ones with hydroxylamine", Abstract XP-002295240, Polish J. of Chem., 1991.

Sen et al., "Search for New Antimalarials. Part V. Synthesis of Some 8-aminoalkylamino- and 8-dialkylaminoalkylamino-chromones", Abstract XP-009035940, J. of the Indian Chem. Soc., Calcutta, pp. 217-222, 1960.

Weng, Lingling, et al., Database Chemabs, "Preparation of Isoflavone Alicyclic Ethers and Oxime Derivatives", Abstact XP-002295241, Materia Medica Inst., Huaxi Med. College, Peop. Rep. China, 1993.

Beugelmans et al., "Action of Hydroxylamine on Chromone and Khellin. Oxime vs. Isoxazoles Structures", XP-002295236, J. of Organic Chem., vol. 42, No. 8, pp. 1356-1360, 1977.

Database Chemab, "Thiazole Analogs of Isoflavones", Abstact XP-002295242, Khimichni ta Biologichni Nauki, 1980.

Spatz et al., "7,2',4'-Trimethoxyflavone", J. of Organic Chem., Abstract XP-002295237, vol. 24, No. 9, pp. 1381-1382, 1959.

Eiden et al., "Uber die Reaktion Von Hydroxylamin Mit 2,6-Dimethyl-3-Acetylchromon", Tetrahedron Letters, Abstract XP-002295238, vol. 17, pp. 1439-1442, 1970.

* cited by examiner

COMPOSITIONS USEFUL AS INHIBITORS OF PROTEIN KINASES

CROSS REFERENCE TO RELATED APPLICATIONS

The present application claims priority under 35 U.S.C. § 119 to U.S. Provisional Application No. 60/460,042 filed Apr. 3, 2003, entitled "Compositions Useful as Inhibitors of Protein Kinases, the entire contents of which is hereby incorporated by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

Cyclin-dependent kinases (CDKs) are serine/threonine protein kinases consisting of a β-sheet rich amino-terminal lobe and a larger carboxy-terminal lobe that is largely α-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active [Meijer, L., *Drug Resistance Updates* 2000, 3, 83-88].

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases [Nigg, E., *Nature Reviews* 2001, 2, 21-32; Flatt, P., Pietenpol, J., *Drug Metabolism Reviews* 2000, 32, 283-305].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the over-expression of cyclin D1 is commonly associated with numerous human cancers including breast, colon, hepatocellular carcinomas and gliomas [Flatt, P., Pietenpol, J., *Drug Metabolism Reviews* 2000, 32, 283-305]. The CDK2/cyclin E complex plays a key role in the progression from the early $G_1$ to S phases of the cell cycle and the overexpression of cyclin E has been associated with various solid tumors. Therefore, inhibitors of cyclins D1, E, or their associated CDKs are useful targets for cancer therapy [Kaubisch, A., Schwartz, G., *The Cancer Journal* 2000, 6, 192-212].

CDKs, especially CDK2, also play a role in apoptosis and T-cell development. CDK2 has been identified as a key regulator of thymocyte apoptosis [Williams, O. et al., *European Journal of Immunology* 2000, 709-713]. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegalovirus, herpes virus, and varicella-zoster virus [Meijer, L., *Drug Resistance Updates* 2000, 3, 83-88].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 [Meijer, L., *Drug Resistance Updates,* 2000 3, 83-88].

The ribosomal protein kinases p70S6K-1 and -2 are members of the AGC sub-family of protein kinases that consists of, amongst others, PKB and MSK. The p70S6 kinases catalyze the phosphorylation and subsequent activation of the ribosomal protein S6, which has been implicated in the translational up-regulation of mRNAs coding for the components of the protein synthetic apparatus.

These mRNAs contain an oligopyrimidine tract at their 5' transcriptional start site, termed a 5'TOP, which has been shown to be essential for their regulation at the translational level (Volarevic, S. et al., *Prog. Nucleic Acid Res. Mol. Biol.* 2001, 65, 101-186). p70 S6K dependent S6 phosphorylation is stimulated in response to a variety of hormones and growth factors primarily via the P13K pathway (Coffer, P. J. et al., *Biochem. Biophys. Res. Commun.*, 1994 198, 780-786), which maybe under the regulation of mTOR, since rapamycin acts to inhibit p70S6K activity and blocks protein synthesis, specifically as a result of a down-regulation of translation of these mRNA's encoding ribosomal proteins (Kuo, C. J. et al., *Nature* 1992, 358, 70-73).

In vitro PDK1 catalyses the phosphorylation of Thr252 in the activation loop of the p70 catalytic domain, which is indispensable for p70 activity (Alessi, D. R., *Curr. Biol.*, 1998, 8, 69-81). The use of rapamycin and gene deletion studies of dp70S6K from Drosophila and p70S6K1 from mouse have established the central role p70 plays in both cell growth and proliferation signaling.

A family of type III receptor tyrosine kinases including Flt3, c-Kit, PDGF-receptor and c-Fms play an important role in the maintenance, growth and development of hematopoietic and non-hematopoietic cells. [Scheijen, B., Griffin J. D., *Oncogene*, 2002, 21, 3314-3333 and Reilly, J. T., *British Journal of Haematology*, 2002, 116, 744-757]. FLT-3 and c-Kit regulate maintenance of stem cell/early progenitor pools as well the development of mature lymphoid and myeloid cells [Lyman, S., Jacobsen, S., *Blood*, 1998, 91, 1101-1134]. Both receptors contain an intrinsic kinase domain that is activated upon ligand-mediated dimerization of the receptors. Upon activation, the kinase domain induces autophosphorylation of the receptor as well as the phosphorylation of various cytoplasmic proteins that help propagate the activation signal leading to growth, differentiation and survival. Some of the downstream regulators of FLT-3 and c-Kit receptor signaling include, PLCγ, PI3-kinase, Grb-2, SHIP and Src related kinases [Scheijen, B., Griffin J. D., *Oncogene*, 2002, 21, 3314-3333]. Both receptor tyrosine kinases have been shown to play a role in a variety of hematopoietic and non-hematopoietic malignancies. Mutations that induce ligand independent activation of FLT-3 and c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-3 or c-Kit can contribute to the malignant phenotype [Scheijen, B., Griffin J. D., *Oncogene*, 2002, 21, 3314-3333].

Glycogen synthase kinase-3 (GSK-3) is a serine/threonine protein kinase comprised of α and β isoforms that are each encoded by distinct genes [Coghlan et al., *Chemistry & Biology*, 2000 7, 793-803; Kim and Kimmel, *Curr. Opinion Genetics Dev.*, 2000, 10, 508-514]. GSK-3 has been implicated in various diseases including diabetes, Alzheimer's disease, CNS disorders such as manic depressive disorder and neurodegenerative diseases, and cardiomyocyte hypertrophy [see, e.g., WO 99/65897; WO 00/38675; Kaytor and Orr, *Curr. Opin. Neurobiol.*, 2000, 12, 275-8; Haq et al., *J. Cell Biol.*, 2000, 151, 117-30; Eldar-Finkelman, *Trends Mol. Med.*, 2000, 8, 126-32]. These diseases are associated with the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor e1F-2B, as well as ATP citrate lyase, axin, heat shock factor-1, c-Jun, c-myc, c-myb, CREB, and CEPBα. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. GSK-3 is a negative regulator of the insulin-induced signal in this pathway. Normally, the presence of insulin causes inhibition of GSK-3-mediated phosphorylation and deactivation of glycogen synthase. The inhibition of GSK-3 leads to increased glycogen synthesis and glucose uptake [Klein et al., *PNAS*, 1996, 93, 8455-9; Cross et al., *Biochem. J.*, 1994, 303, 21-26; Cohen, *Biochem. Soc. Trans.*, 1993, 21, 555-567; and Massillon et al., *Biochem. J.* 1994, 299, 123-128; Cohen and Frame, *Nat. Rev. Mol. Cell. Biol.*, 2001, 2, 769-76]. However, where the insulin response is impaired in a diabetic patient, glycogen synthesis and glucose uptake fail to increase despite the presence of relatively high blood levels of insulin. This leads to abnormally high blood levels of glucose with acute and chronic effects that may ultimately result in cardiovascular disease, renal failure and blindness. In such patients, the normal insulin-induced inhibition of GSK-3 fails to occur. It has also been reported that GSK-3 is overexpressed in patients with type II diabetes [WO 00/38675]. Therapeutic inhibitors of GSK-3 are therefore useful for treating diabetic patients suffering from an impaired response to insulin.

Apoptosis has been implicated in the pathophysiology of ischemic brain damage (Li et al., 1997; Choi, et al., 1996; Charriaut-Marlangue et al., 1998; Grahm and Chen, 2001; Murphy et al., 1999; Nicotera et al., 1999). Recent publications indicate that activation of GSK-3β may be involved in apoptotic mechanisms (Kaytor and Orr, 2002; Culbert et al., 2001). Studies in rat models of ischemic stroke induced by middle cerebral artery occlusion (MCAO) showed increased GSK-3β expression is following ischemia (Wang et al., *Brain Res.*, 2000, 859, 381-5; Sasaki et al., *Neurol Res.*, 2001, 23, 588-92). Fibroblast growth factor (FGF) reduced ischemic brain injury after permanent middle cerebral artery occlusion (MCO) in rats (Fisher et al. 1995; Song et al. 2002). Indeed, the neuroprotective effects of FGF demonstrated in ischemia models in rats may be mediated by a PI-3 kinase/AKT-dependent inactivation of GSK-3β (Hashimoto et al., 2002). Thus, inhibition of GSK-3β after a cerebral ischemic event may ameliorate ischemic brain damage.

GSK-3 is also implicated in mycardial infarction. See Jonassen et al., *Circ. Res.*, 2001, 89, 1191 (the reduction in myocardial infarction by insulin administration at reperfusion is mediated via Akt dependent signaling pathway.); Matsui et al., *Circulation*, 2001, 104, 330 (Akt activation preserves cardiac finction and prevents cardiomyocyte injury after transient cardiac ischemia in vivo); Miao et al., *J. Mol. Cell. Cardiol.*, 2000, 32, 2397 (intracoronary, adenovirus-mediated Akt gene delivery in heart reduced gross infarct size following ischemia-reperfusion injury in vivo); and Fujio et al., *Circulation*, 2000, 101, 660 (Akt signaling inhibits cardiac myocyte apoptosis in vitro and protects against ischemia-reperfusion injury in mouse heart).

GSK-3 activity plays a role in head trauma. See Noshita et al., *Neurobiol. Dis.*, 2002, 9, 294 (upregulation of Akt/PI3-kinase pathway may be crucial for cell survival after traumatic brain injury) and Dietrich et al., *J. Neurotrauma,* 1996, 13, 309 (posttraumatic administration of bFGF significantly reduced damaged cortical neurons & total contusion volume in a rat model of traumatic brain injury).

GSK-3 is also known to play a role in psychiatric disorders. See Eldar-Finkelman, *Trends Mol. Med.,* 2002, 8, 126; Li et al., *Bipolar Disord.,* 2002, 4, 137 (LiCl and Valproic acid, anti-psychotic, mood stabilizing drugs, decrease GSK-3 activities and increase beta-catenin) and Lijam et al., *Cell,* 1997, 90, 895 (dishevelled KO mice showed abnormal social behavior and defective sensorimotor gating. Dishevelled, a cytoplamic protein involved in WNT pathway, inhibits GSK-3beta activities).

It has been shown that GSK-3 inhibition by lithium and valproic acid induces axonal remodeling and change synaptic connectivity. See Kaytor & Orr, *Curr. Opin. Neurobiol.,* 2002, 12, 275 (downregulation of GSK-3 causes changes in microtubule-associated proteins: tau, MAP1 & 2) and Hall et al., *Mol. Cell. Neurosci.,* 2002, 20, 257 (lithium and valproic acid induces the formation of growth cone-like structures along the axons).

GSK-3 activity is also associated with Alzheimer's disease. This disease is characterized by the presence of the well-known β-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Curr. Biol.,* 1994, 4, 1077-86; and Brownlees et al., *Neuroreport,* 1997, 8, 3251-55; Kaytor and Orr, *Curr. Opin. Neurobiol.,* 2000, 12, 275-8]. In transgenic mice overexpressing GSK-3, a significant increase in Tau hyperphosphorylation and abnormal morphology of neurons was observed [Lucas et al., *EMBO J.,* 2001, 20, 27-39]. Active GSK-3 accumulates in cytoplasm of pretangled neurons, which can lead to neurofibrillary tangles in brains of patients with AD [Pei et al., *J. Neuropathol. Exp. Neurol.,* 1999, 58, 1010-19]. Therefore, inhibition of GSK-3 slows or halts the generation of neurofibrillary tangles and thus can treat or reduce the severity of Alzheimer's disease.

Evidence for the role GSK-3 plays in Alzheimer's disease has been shown in vitro. See Aplin et al., *J. Neurochem.* 1996, 67, 699; Sun et al., *Neurosci. Lett.* 2002, 321, 61 (GSK-3b phosphorylates cytoplasmic domain of Amyloid Precursor Protein (APP) and GSK-3b inhibition reduces Ab40 & Ab42 secretion in APP-transfected cells); Takashima et al., *PNAS,* 1998, 95, 9637 (1998); Kirschenbaum et al., *J. Biol. Chem.,* 2001, 276, 7366 (GSK-3b complexes with and phosphorylates presenilin-1, which is associated with gamma-secretase activity in the synthesis of Aβ from APP); Takashima et al., *Neurosci. Res.* 1998, 31, 317 (activation of GSK-3b by Ab(25-35) enhances phosphorylation of tau in hippocampal neurons. This observation provides a link between Aβ and neurofibrillary tangles composed of hyperphosphorylated tau, another pathological hallmark of AD); Takashima et al., *PNAS,* 1993, 90, 7789 (blockade of GSK-3b expression or activity prevents Ab-induced neurodegeneration of cortical and hippocampal primary cultures); Suhara et al., *Neurobiol. Aging,* 2003, 24, 437 (intracellular Ab42 is toxic to endothelial cells by interfering with activation of the Akt/GSK-3b signaling-dependent mechanism); De Ferrari et al., *Mol. Psychiatry,* 2003, 8, 195 (lithium protects N2A cells & primary hippocampal neurons from Aβ fibril-induced cytotoxicity, & reduces nuclear translocation/destabilization of b-catenin); and Pigino et al., *J. Neurosci.,* 2003, 23, 4499 (the mutations in Alzheimer's presenilin 1 may deregulate and increase GSK-3 activity, which in turn, impairs axonal transport in neurons. The consequent reductions in axonal transport in affected neurons can ultimately lead to neurodegeneration).

Evidence for the role GSK-3 plays in Alzheimer's disease has been shown in vivo. See Yamaguchi et al., *Acta Neuropathol.,* 1996, 92, 232; Pei et al., *J. Neuropath. Exp. Neurol.* 1999, 58, 1010 (GSK-3b immunoreactivity is elevated in susceptible regions of AD brains); Hernandez et al., *J. Neurochem.,* 2002, 83, 1529 (transgenic mice with conditional GSK-3b overexpression exhibit cognitive deficits similar to those in transgenic APP mouse models of AD); De Ferrari et al., *Mol. Psychiatry,* 2003, 8, 195 (chronic lithium treatment rescued neurodegeneration and behavioral impairments (Morris water maze) caused by intrahippocampal injection of Aβ fibrils.); McLaurin et al., *Nature Med.,* 2002, 8, 1263 (Immunization with Aβ in a transgenic model of AD reduces both AD-like neuropathology and the spatial memory impairments); and Phiel et al., *Nature,* 2003, 423, 435 (GSK-3 regulates amyloid-beta peptide production via direct inhibition of gamma secretase in AD tg mice).

Presenilin-1 and kinesin-1 are also substrates for GSK-3 and relate to another mechanism for the role GSK-3 plays in Alzheimer's disease, as was recently described by Pigino, G., et al., *Journal of Neuroscience,* 2003, 23, 4499. It was found that GSK-3beta phosphorylates kinesin-I light chain, which results in a release of kinesin-1 from membrane-bound organelles, leading to a reduction in fast anterograde axonal transport (Morfini et al., 2002). The authors suggest that the mutations in PS1 may deregulate and increase GSK-3 activity, which in turn, impairs axonal transport in neurons. The consequent reductions in axonal transport in affected neurons ultimately leads to neurodegeneration.

GSK-3 is also associated with amyotrophic lateral sclerosis (ALS). See Williamson and Cleveland, 1999 (Axonal transport is retarded in a very early phase of ALS in mSOD1 mice); Morfini et al., 2002 (GSK3 phosphorylates kinesin light chains and inhibit anterograde axonal transport); Warita et al., *Apoptosis,* 2001, 6, 345 (2001) (The majority of spinal motor neurons lost the immunoreactivities for both PI3-K and Akt in the early and presymptomatic stage that preceded significant loss of the neurons in this SOD1 tg animal model of ALS); and Sanchez et al., 2001 (The inhibition of PI-3K induces neurite retraction mediated by GSK-3 activation).

GSK-3 activity is also linked to spinal cord and peripheral nerve injuries. It has been shown that GSK-3 inhibition by lithium and valproic acid can induce axonal remodeling and change synaptic connectivity. See Kaytor & Orr, *Curr. Opin. Neurobiol.,* 2002, 12, 275 (downregulation of GSK-3 causes changes in microtubule-associated proteins: tau, MAP1 & 2) and Hall et al., *Mol. Cell. Neurosci.,* 2002, 20, 257 (lithium and valproic acid induces the formation of growth cone-like structures along the axons). See also Grothe et al., *Brain Res.,* 2000, 885, 172 (FGF-2 stimulates Schwann cell proliferation and inhibits myelination during axonal growth); Grothe and Nikkhah, 2001 (FGF-2 is up regulated in the proximal and distal nerve stumps within 5 hours after nerve crush); and Sanchez et al., 2001 (The inhibition of PI-3K induces neurite retraction mediated by GSK-3 activation).

Another substrate of GSK-3 is β-catenin, which is degraded after phosphorylation by GSK-3. Reduced levels of β-catenin have been reported in schizophrenic patients and have also been associated with other diseases related to increase in neuronal cell death [Zhong et al., *Nature,* 1998, 395, 698-702; Takashima et al., *PNAS,* 1993, 90, 7789-93; Pei et al., *J. Neuropathol. Exp.,* 1997, 56, 70-78; and Smith et al., *Bioorg. Med. Chem.* 2001, 11, 635-639]. Furthermore, β-catenin and Tcf-4 play a dual role in vascular remodeling by inhibiting vascular smooth muscle cell apoptosis and promoting proliferation (Wang et al., *Circ. Res.*, 2002, 90, 340. Accordingly, GSK-3 is associated with angiogenic disorders. See also Liu et al., *FASEB J.*, 2002, 16, 950 (activation of GSK-3 reduces hepatocyte growth factor, leading to altered endothelial cell barrier function and diminished vascular integrity.) and Kim et al., *J. Biol. Chem.*, 2002, 277, 41888 (GSK-3beta activation inhibits angiogenesis in vivo using a Matrigel plug assay: the inhibition of GSK-3beta signalling enhances capillary formation).

Association between GSK-3 and Huntington's disease has been shown. See Carmichael et al., *J. Biol. Chem.*, 2002, 277, 33791 (GSK-3beta inhibition protect cells from polyglutamine-induced neuronal and non-neuronal cell death via increases in b-catenin and its associated transcriptional pathway). Overexpression of GSK-3 reduced the activation of heat shock transcription factor-1 and heat shock protein HSP70 (Bijur et al., *J. Biol. Chem.*, 2000, 275, 7583 that are shown to decrease both poly-(Q) aggregates and cell death in in vitro HD model (Wyttenbach et al., *Hum. Mol. Genet.*, 2002, 11, 1137).

GSK-3 effects the levels of FGF-2 and their receptors which are increased during remyelination of brain aggregate cultures in remyelinating rat brains. See Copelman et al., 2000, Messersmith, et al., 2000; and Hinks and Franklin, 2000. It was also found that FGF-2 induces process outgrowth by oligodendrocytes implicating involvement of FGF in remyelination (Oh and Yong, 1996; Gogate et al., 1994) and that FGF-2 gene therapy has shown to improve the recovery of experimental allergic encephalomyelitis (EAE) mice (Ruffini, et al., 2001).

GSK-3 has also been associated with hair growth because Wnt/beta-catenin signaling is shown to play a major role in hair follicle morphogenesis and differentiation (Kishimotot et al., *Genes Dev.*, 2000, 14, 1181; Millar, *J. Invest. Dermatol.*, 2002, 118, 216). It was found that mice with constituitive overexpression of the inhibitors of Wnt signaling in skin failed to develop hair follicles. Wnt signals are required for the initial development of hair follicles and GSK-3 constituitively regulates Wnt pathways by inhibiting beta-catenin. (Andl et al., *Dev. Cell*, 2002, 2, 643). A transient Wnt signal provides the crucial initial stimulus for the start of a new hair growth cycle, by activating beta-catenin and TCF-regulated gene transcription in epithelial hair follicle precursors (Van Mater et al., *Genes Dev.*, 2003, 17, 1219).

Because GSK-3 activity is associated with sperm motility, GSK-3 inhibition is useful as a male contraceptive. It was shown that a decline in sperm GSK-3 activity is associated with sperm motility development in bovine and monkey epididymis. (Vijayaraghavan et al., *Biol. Reprod.*, 1996, 54, 709; Smith et al., *J. Androl.*, 1999, 20, 47). Furthermore, tyrosine & serine/threonine phosphorylation of GSK-3 is high in motile compared to immotile sperm in bulls (Vijayaraghavan et al., *Biol. Reprod.*, 2000, 62, 1647). This effect was also demonstrated with human sperm (Luconi et al., *Human Reprod.*, 2001, 16, 1931).

Interleukin-1 receptor-associated kinase-4 (IRAK-4) is a 53 kDa member of the IRAK family of serine-threonine kinases. Within the family IRAK-4 and IRAK-1 appear to have finctional kinase domains while IRAK-2 and IRAK-m do not (Janssens S, Beyaert R., *Mol. Cell.* 2003 11, 293-302).

IRAK-4 is important for the innate and adaptive immune responses. It plays a major role in cellular responses to immune system modulators, finctioning in signal transduction from activated members of the interleukin-1 receptor/ Toll-like receptor (IL-1R/TLR) superfamily (Li, S. et al., *Proc Natl. Acad. Sci. USA.* 2002 99, 5567-5572; Suzuki, N., et al., *J. Immunol.* 2003 170, 4031-4035). IRAK-4 also has effects outside of the immune system such as influencing neurotrophin-driven neuronal survival (Mamidipudi, V. et al., *J. Biol. Chem.* 2002 277, 28010-28018). Upon binding proinflammatory cytokines IL-1 and IL-18 or pathogen-associated molecular pattern (PAMPs) ligands (eg. LPS, viral RNA, lipoproteins/peptidoglycans, etc.) their cognate receptors (IL-1R, IL-18R, and TLR receptor family, respectively) recruit a series of adaptors. IRAK-4 interacts with the resultant complex and propagates the activation signal through a series of additional proteins that ultimately stimulate IkappaB kinases (IKKs) and the mitogen-activated protein kinases (MAPKs), JNK and p38. These kinases stimulate NFkappaB- and AP-1-dependent transcription, the products of which are important for controlling processes such as cell survival and proinflammatory cytokine production (Yamamoto, Y. and Gaynor, R. B. et al., *J. Clin. Invest.* 2001 107, 135-142; Dunne, A. and O'Neill, L A J., *Sci. STKE* Feb. 25; 2003 (171):re3). Mice lacking IRAK-4 do not respond to IL-1 and ligands that stimulate various TLR's and are resistant to certain immunological challenges (Suzuki, N et al., *Nature* 2002 416, 750-756).

Activators of the IL-1R/TLR family contribute to a variety of diseases including inflammation and cancer (O'Neill L A., *Sci STKE.* Aug. 8; 2000 (44):RE1; Apte, R N. and Voronov, E., Semin, *Cancer Biol.* 2002 12, 277-290; Apte, R N. et al., *Adv. Exp. Med. Biol.* 2000 479, 277-88). IL-1 and IL-18 are important mediators of inflammatory diseases (Dinarello C A, *Clin. Exp. Rheumatol.* 2002: 20 (5 Suppl 27): S1-13) including rheumatoid arthritis (Dayer, J M, Rheumatology (Oxford), 2003 42, Suppl 2:ii3-10; Dai, S M., et al., *Arthritis Rheum.* 2004 50, 432-443) and inflammatory bowel disease (Lochner, M. and Forster, I., *Pathobiology*, 2002-2003 70, 164-169). TLR4 ligands such as LPS (O'Neill, L A J, *Curr. Opin. Pharmacol.* 2003 3, 396-403), hsp60 (Ohashi, K. et al., *J. Immunol.* 2000 164, 558-561), and fibronectin fragments (Okamura, Y. et al., *J. Biol. Chem.* 2001 276, 10229-10233) promote processes associated with the inflammatory response. Other diseases affected by TLR family may include autoimmunity (Eriksson, U., et al., *Nat. Med.* 2003 9, 1484-1490), viral infections (Vaidya, S. A. and Cheng, G., *Curr. Opin. Immunol.* 2003 15, 402-407; Tabeta K., et al., *Proc. Natl. Acad. Sci. USA*, 2004 101, 3516-3521; Diebold, S. S., et al., *Science*, 2004 303, 1529-1531), and sepsis (Cristofaro, P. and Opal, S. M. *Expert Opin. Ther. Targets*, 2003 7, 603-612).

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank, *Mol. Med.* 1999, 5, 432-456 and Seidel et al., *Oncogene* 2000, 19, 2645-2656].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al., *Blood* 2000, 96, 2172-2180].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al., *Nature* 1990, 346, 274-276 and Galli, N. *Engl. J. Med.* 1993, 328, 257-265]. A crucial role for JAK3 in IgE receptor-mediated mast cell responses in vitro and in vivo has been established [Malaviya et al., *Biochem. Biophys. Res. Commun.* 1999, 257, 807-813]. In addition, the prevention of type I hypersensitivity reactions, including anaphylaxis, mediated by mast cell-activation through inhibition of JAK3 has also been reported [Malaviya et al., *J. Biol. Chem.* 1999, 274, 27028-27038]. Targeting mast cells with JAK3 inhibitors modulated mast cell degranulation in vitro and prevented IgE receptor/antigen-mediated anaphylactic reactions in vivo.

A recent study described the successful targeting of JAK3 for immunosuppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, *Transpl. Proc.* 2001, 33, 3268-3270].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demostrated that IL-4-mediated activation of IL-4/STAT pathway is mediated through the Janus Kinases (JAK 1 & 3) and that IL-4-associated JAK kinases are expressed in the RA synovium [Muller-Ladner et al., *J. Immunol.* 2000, 164, 3894-3901].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu et al., *Biochem. Biophys. Res. Commun.* 2000, 267, 22-25].

Signal transducer and activator of transcription (STAT) proteins are activated by, among others, the JAK family kinases. Results from a recent study suggested the possibility of intervention in the JAK/STAT signaling pathway by targeting JAK family kinases with specific inhibitors for the treatment of leukemia [Sudbeck et al., *Clin. Cancer Res.* 1999, 5, 1569-1582]. JAK3 specific compounds were shown to inhibit the clonogenic growth of JAK3-expressing cell lines DAUDI, RAMOS, LC1-19, NALM-6, MOLT-3 and HL-60.

In animal models, TEL/JAK2 fusion proteins have induced myeloproliferative disorders and in hematopoietic cell lines, and introduction of TEL/JAK2 resulted in activation of STAT1, STAT3, STAT5, and cytokine-independent growth [Schwaller et al., *EMBO J.* 1998, 17, 5321-5333].

Inhibition of JAK3 and TYK2 abrogated tyrosine phosphorylation of STAT3, and inhibited cell growth of mycosis fungoides, a form of cutaneous T-cell lymphoma. These results implicated JAK family kinases in the constitutively activated JAK/STAT pathway that is present in mycosis fungoides [Nielsen et al., *Proc. Nat. Acad. Sci. U.S.A.* 1997, 94, 6764-6769]. Similarly, STAT3, STAT5, JAK1 and JAK2 were demonstrated to be constitutively activated in mouse T-cell lymphoma characterized initially by LCK over-expression, thus further implicating the JAK/STAT pathway in abnormal cell growth [Yu et al., *J. Immunol.* 1997, 159, 5206-5210]. In addition, IL-6-mediated STAT3 activation was blocked by an inhibitor of JAK, leading to sensitization of myeloma cells to apoptosis [Catlett-Falcone et al., *Immunity* 1999, 10, 105-115].

The c-met proto-oncogene encodes the Met receptor tyrosine kinase. The Met receptor is a 190 kDa glycosylated dimeric complex composed of a 50 kDa alpha chain disulfide-linked to a 145 kDa beta chain. The alpha chain is found extracellularly while the beta chain contains transmembrane and cytosolic domains. Met is synthesized as a precursor and is proteolytically cleaved to yield mature alpha and beta subunits. It displays structural similarities to semaphorins and plexins, a ligand-receptor family that is involved in cell-cell interaction. The ligand for Met is hepatocyte growth factor (HGF), a member of the scatter factor familyand has some homology to plaminogen [Longati, P. et al., *Curr. Drug Targets* 2001, 2, 41-55); Trusolino, L. and Comoglio, P. *Nature Rev. Cancer* 2002, 2, 289-300].

Met appears to be functioning in tumorigenesis and tumor metastasis. Chromosomal rearrangements forming Tpr-met fusions in an osteoclast cell line resulted in constitutively active Met receptors and transformation (Cooper, C. S. et al., *Nature* 1984, 311, 29-33). Met mutants exhibiting enhanced kinase activity have been identified in both hereditary and sporadic forms of papillary renal carcinoma (Schmidt, L. et al., *Nat. Genet.* 1997, 16, 68-73; Jeffers, M. et al., *Proc. Nat. Acad. Sci.* 1997, 94, 11445-11500). Expression of Met along with its ligand HGF is transforming, tumorigenic, and metastatic (Jeffers, M. et al., *Oncogene* 1996, 13, 853-856; Michieli, P. et al., *Oncogene* 1999, 18, 5221-5231). HGF/Met has been shown to inhibit anoikis, suspension-induced programmed cell death (apoptosis), in head and neck squamous cell carcinoma cells. Anoikis resistance or anchorage-independent survival is a hallmark of oncogenic transformation of epithelial cells (Zeng, Q. et al., *J. Biol. Chem.* 2002, 277, 25203-25208).

HGF/Met signaling is involved in cell adhesion and motility in normal cells and plays a major role in the invasive growth that is found in most tissues, including cartilage, bone, blood vessels, and neurons (reviewed in Comoglio, P. M. and Trusolino, L. *J. Clin. Invest.* 2002, 109, 857-862). Dysfunctional activation or increased numbers of Met is likely to contribute to the aberrant cell-cell interactions that lead to migration, proliferation, and survival of cells that is characteristic of tumor metastasis. Activation of Met induces and sustains a variety of tumors [Wang, R. et al., *J. Cell. Biol.* 2001, 153, 1023-1034; Liang, T. J. et al., *J. Clin. Invest.* 1996, 97, 2872-2877; Jeffers, M. et al., *Proc. Nat. Acad. Sci.* 1998, 95, 14417-14422] while loss of Met inhibits growth and invasiveness of tumor cells [Jiang, W. G. et al., *Clin. Cancer Res.* 2001, 7, 2555-2562; Abounader, R. et al., *FASEB J.* 2002 16, 108-110]. Increased expression of Met/HGF is seen in many metastatic tumors including colon (Fazekas, K. et al., *Clin. Exp. Metastasis* 2000, 18, 639-649), breast (Elliott, B. E. et al., 2002, *Can. J. Physiol. Pharmacol.* 80, 91-102), prostate (Knudsen, B. S. et al., *Urology* 2002, 60, 1113-1117), lung (Siegfried, J. M. et al., *Ann. Thorac. Surg.* 1998, 66, 1915-1918), and gastric (Amemiya, H. et al., *Oncology* 2002, 63, 286-296).

HGF-Met signaling has also been associated with increased risk of atherosclerosis (Yamamoto, Y. et al., *J. Hypertens.* 2001, 19, 1975-1979; Morishita, R. et al., *Endocr. J.* 2002, 49, 273-284) and increased fibrosis of the lung (Crestani, B. et al., *Lab. Invest.* 2002, 82, 1015-1022.

Syk is a tyrosine kinase that plays a critical role in FcεERI mediated mast cell degranulation and eosinophil activation. Accordingly, Syk kinase is implicated in various allergic disorders, in particular asthma. It has been shown that Syk binds to the phosphorylated gamma chain of the FceRI receptor via N-terminal SH2 domains and is essential for downstream signaling [Taylor et al., *Mol. Cell. Biol.* 1995, 15, 4149].

Inhibition of eosinophil apoptosis has been proposed as a key mechanism for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense) [Yousefi et al., *J. Exp. Med.* 1996, 183, 1407].

The role of Syk in FcγR dependent and independent response in bone marrow derived macrophages has been determined by using irradiated mouse chimeras reconstituted with fetal liver cells from Syk −/− embryos. Syk deficient macrophages were defective in phagocytosis induced by FcγR but showed normal phagocytosis in response to complement [Kiefer et al., *Mol. Cell. Biol.* 1998, 18, 4209]. It has also been reported that aerosolized Syk antisense suppresses Syk expression and mediator release from macrophages [Stenton et al., *J. Immunology* 2000, 164, 3790].

ZAP-70 is essential for T-cell receptor signalling. Expression of this tyrosine kinase is restricted to T-cells and natural killer cells. The importance of ZAP-70 in T-cell function has been demonstrated in human patients, human T-cell lines and mice. Human patients suffering from a rare form of severe combined deficiency syndrome (SCID) possess homozygous mutations in ZAP-70 (reviewed in *Elder J. of Pedriatric Hematology/Oncology* 1997, 19(6), 546-550). These patients have profound immunodeficiency, lack CD8+ T-cells and have CD4+ T-cells that are unresponsive to T-cell receptor (TCR)-mediated stimulation. Following TCR activation these CD4+ cells show severe defects in Ca2+ mobilization, tyrosine phosphorylation of down-stream substrates, proliferation and IL-2 production 70 (reviewed in *Elder Pedriatric Research* 39, 743-748). Human Jurkat cells lacking ZAP-70 also provide important insights into the critical role of ZAP-70 in T-cell receptor signalling. A Jurkat clone (p116) with no detectable ZAP-70 protein was shown to have defects in T-cell receptor signalling which could be corrected by re-introduction of wild type ZAP-70 (Williams et al., *Molecular and Cellular Biology* 1998, 18 (3), 1388-1399). Studies of mice lacking ZAP-70 also demonstrate a requirement of ZAP-70 in T-cell receptor signalling. ZAP-70-deficient mice have profound defects in T-cell development and T-cell receptor signalling in thymocytes is impaired (Negishi et al., *Nature* 1995 376, 435-438).

The importance of the kinase domain in ZAP-70 function is demonstrated by studies of human patients and mice expressing identical mutations in the DLAARN motif within the kinase domain of ZAP-70. Inactivation of kinase activity by this mutation results in defective T-cell receptor signalling (Elder et al., *J. Immunology* 2001, 656-661). Catalytically inactive ZAP-70 (Lys369Arg) was also defective in restoring T-cell receptor signalling in a ZAP-70 deficient Jurkat cell clone (p116) (Williams et al., *Molecular and Cellular Biology* 1998, 18 (3), 1388-1399).

Transforming growth factor-beta (TGF-beta) activated kinase 1 (TAK-1) is a 67 kDa ubiquitin-dependent serine-threonine kinase that functions as a mitogen-activated protein (MAP) kinase kinase kinase (MAPKKK or MEKK) (Wang, C., et al., Nature 2001, 412, 346-351).

Originally described as stimulated by TGF-beta superfamily members (Yamaguchi K. et al., Science 1995, 270, 2008-2011) TAK-1 is known to also function in signaling from numerous cell modulators including proinflammatory cytokines. TAK-1 is critical for signaling from IL-1beta/TLR ligands (Holtmann H, et al., J. Biol. Chem. 2001, 276, 3508-3516; Jiang Z, et al., J. Biol. Chem. 2003, 278, 16713-16719) and TNF-alpha (Takaesu G. et al., J. Mol. Biol. 2003, 326, 105-115). In addtion TAK-1 plays a role in IL-18 (Wald, D., et al., Eur. J. Immunol. 2001, 31, 3747-3754), RANKL (Mizukami J., et al., Mol. Cell. Biol. 2002, 22, 992-1000) and ceramide (Shirakabe K., et al., J. Biol. Chem. 1997, 272, 8141-8144) signaling.

Through interaction with corresponding cell surface receptors these ligands stimulate TAK-1 to relay signals to a variety of pathways such as IKK/NFkappaB, JNK, and p38, that are important regulators of cellular processes including apoptosis (Edlund S., et al., Mol Biol Cell. 2003, 14, 529-544), differentiation (Suzawa, M. et al., Nat Cell Biol 2003, 5, 224-230), and cell cycle progression (Bradham C A, et al., Am J Physiol Gastrointest Liver Physiol. 2001 281, G1279-89).

Modification of signaling pathways can alter cellular processes and contribute to disease. Due to its central role in signaling from numerous cell surface receptors TAK-1 may be an important therapeutic target for a variety of diseases. The cytokines IL-1beta and TNFalpha are important mediators of inflammation in rheumatoid arthritis and other inflammatory diseases (Maini R N. and Taylor P C. Ann. Rev. Med. 2000, 51, 207-229). TAK-1 may be important in regulating disease-relevant cellular responses in these cases (Hammaker D R, et al. J. Immunol. 2004, 172, 1612-1618). TAK-1 affects cellular fibrotic responses (Ono K., et al., Biochem. Biophys. Res. Commun. 2003, 307, 332-337). It may also plays a role in heart failure (Zhang, D., Nat. Med. 2000, 6, 556-563), osteoporosis (Mizukami J, et al., Mol. Cell. Biol. 2002, 22, 992-1000) and survival of hepatocellular carcinoma cells (Arsura M, et al. Oncogene 2003, 22, 412-425). TAK-1 signaling may affect neurite outgrowth (Yanagisawa M., et al. Genes Cells. 2001, 6, 1091-1099) and is involved in control of adipogenesis (Suzawa M., et al. Nat. Cell. Biol. 2003, 5, 224-230) and cardiomyocyte differentiation (Monzen K., et al. J. Cell. Biol. 2001, 153(4), 687-698.

Accordingly, there is a great need to develop compounds useful as inhibitors of protein kinases. In particular, it would be desirable to develop compounds that are useful as inhibitors of CDK-2, cMET, FLT-3, JAK-3, GSK-3, IRAK-4, SYK, p70S6K, TAK-1, and ZAP-70 particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of CDK-2, cMET, FLT-3, JAK-3, GSK-3, IRAK-4, SYK, p70S6K, TAK-1, and ZAP-70 protein kinase. These compounds have the general formula I:

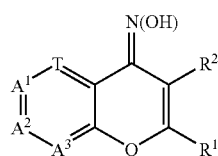

or a pharmaceutically acceptable salt or mixtures thereof, wherein $R^1$, $R^2$, T, $A^1$, $A^2$, and $A^3$ are as defined below.

These compounds and pharmaceutically acceptable compositions thereof are useful for treating or preventing a variety of diseases, disorders or conditions, including, but not limited to cancer, heart disease, diabetes, Alzheimer's disease, immunodeficiency disorders, inflammatory diseases, allergic diseases, autoimmune diseases, destructive bone disorders such as osteoporosis, proliferative disorders, infectious diseases, immunologically-mediated diseases, neurodegenerative or neurological disorders, or viral diseases. The compositions are also useful in methods for preventing cell death and hyperplasia and therefore may be used to treat or prevent reperfusion/ischemia in stroke, heart attacks, and organ hypoxia.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

I. General Description of Compounds of the Invention

The present invention relates to a compound of formula I:

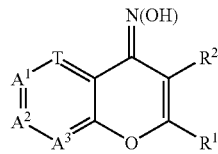

or a pharmaceutically acceptable salt or mixtures thereof, wherein:

$R^1$ is -(L)$_m$R, -(L)$_m$Ar$^1$, or -(L)$_m$Cy$^1$;

L is —S—, —O—, —N(R)—, or a $C_{1-6}$ alkylidene chain wherein up to two non-adjacent methylene units of L are optionally and independently replaced by —S—, —O—, —N(R)—, —N(R)C(O)—, —N(R)C(S)—, —N(R)C(O)N(R)—, —N(R)C(S)N(R)—, —N(R)CO$_2$—, —C(O)—, —CO$_2$—, —C(O)N(R)—, —C(S)N(R)—, —OC(O)N(R)—, —SO$_2$—, —SO$_2$N(R)—, —N(R)SO$_2$—, —N(R)SO$_2$N(R)—, —C(R)=NN(R)—, —C(R)=N—O(R)—, —C(O)C(O)—, or —C(O)CH$_2$C(O)—;

m is 0 or 1;

Ar$^1$ is an optionally substituted 5-7 membered monocyclic ring or an 8-10 membered bicyclic ring having 0-5 heteroatoms independently selected from nitrogen, oxygen, or sulfur;

Cy$^1$ is an optionally substituted 3-7 membered saturated or partially unsaturated monocyclic ring having 0-3 heteroatoms independently selected from nitrogen, oxygen, or sulfur, or an 8-10 membered saturated or partially unsaturated bicyclic ring system having 0-5 heteroatoms independently selected from nitrogen, oxygen, or sulfur, wherein;

Ar$^1$ and Cy$^1$ are each optionally substituted with up to 5 occurrences of Z-R$^X$; wherein each occurrence of Z is independently a bond or a $C_{1-6}$ alkylidene chain, wherein up to two non-adjacent methylene units of Z are optionally replaced by —S—, —O—, —N(R)—, —N(R)C(O)—, —N(R)C(S)—, —N(R)C(O)N(R)—, —N(R)C(S)N(R)—, —N(R)CO$_2$—, —C(O)—, —CO$_2$—, —C(O)N(R)—, —C(S)N(R)—, —OC(O)N(R)—, —SO$_2$—, —SO$_2$N(R)—, —N(R)SO$_2$—, —N(R)SO$_2$N(R)—, —C(R)=NN(R)—, —C(R)=N—O(R)—, —C(O)C(O)—, or —C(O)CH$_2$C(O)—;

each occurrence of R$^X$ is independently selected from —R', halogen, NO$_2$, CN, —OR', —SR', —N(R')$_2$, —N(R')C(O)R', —N(R')C(S)R', —N(R')C(O)N(R')$_2$, —N(R')C(S)N(R')$_2$, —N(R')CO$_2$R', —C(O)R', —C(S)R', —CO$_2$R', —OC(O)R', —C(O)N(R')$_2$, —C(S)N(R')$_2$, —OC(O)N(R')$_2$, —S(O)R', —SO$_2$R', —S(O)$_3$R'; —SO$_2$N(R')$_2$, —N(R')SO$_2$R', —N(R')SO$_2$N(R')$_2$, —C(O)C(O)R', —C(O)CH$_2$C(O)R', —NR'NR'C(O)R', —NR'NR'C(O)N(R')$_2$, —NR'NR'CO$_2$R', —C(O)N(OR') R', —C(NOR')R', —S(O)$_3$R, —N(OR')R', —C(=NH)—N(R')$_2$; or —(CH$_2$)$_{0-2}$NHC(O)R'; wherein each occurrence of R is independently hydrogen or an optionally substituted $C_{1-6}$ aliphatic group, each occurrence of R' is independently hydrogen or an optionally substituted $C_{1-6}$ aliphatic group, an optionally substituted $C_{6-10}$ aryl ring, an optionally substituted heteroaryl ring having 5-10 ring atoms, or an optionally substituted heterocyclyl ring having 3-10 ring atoms; or R and R' or two occurrences of either R or R' are taken together with the atoms to which they are bound to form an optionally substituted 5-8 membered saturated, partially unsaturated, or aryl ring having 0-4 heteroatoms independently selected from nitrogen, oxygen, or sulfur; or two occurrences of either R' or R on the same nitrogen are taken together with the nitrogen atom to which they are bound to form an optionally substituted 5-8 membered saturated, partially unsaturated, or aryl ring having 1-4 heteroatoms independently selected from nitrogen, oxygen, or sulfur;

$R^2$ is hydrogen, CN, —SR, —OR, —CO$_2$R, —OC(O)R, —C(O)R, —C(O)N(R)$_2$, —N(R)$_2$, —N(R)C(O)R, or an optionally substituted $C_{1-6}$ aliphatic group;

T is selected from nitrogen or CR$^3$;

each of $A^1$, $A^2$, and $A^3$ is independently nitrogen or CR$^4$ provided that no more than two of T, $A^1$, $A^2$, or $A^3$ are nitrogen;

$R^3$ is selected from hydrogen, halogen, NO$_2$, CN, —SR, —OR, —N(R)$_2$, or an optionally substituted $C_{1-6}$ aliphatic group; and $R^4$ is selected from halogen, NO$_2$, CN, -(L)$_m$R, -(L)$_m$Ar$^1$, or -(L)$_m$Cy$^1$; or two R$^4$ groups on adjacent atoms are taken together to form an optionally substituted 5-7 membered partially unsaturated or fully unsaturated ring having 0-3 heteroatoms independently selected from oxygen, sulfur, or nitrogen, wherein;

each ring formed by two R$^4$ groups on adjacent atoms taken together is optionally substituted with up to 4 occurrences of Z-R$^X$.

In certain embodiments, for compounds of formula I, one or more, or all of the following conditions apply:

a) when T is $CR^3$ where $R^3$ is H, and $A^2$ and $A^3$ are both $CR^4$ where $R^4$ is H, $R^2$ is H and $R^1$ is $-(L)_m Ar^1$, m is zero, and $Ar^1$ is phenyl, 4-OH phenyl, 3-$NO_2$ phenyl, 4-OMe phenyl, 4-Me phenyl, or 1,2 ethylenedioxy phenyl, then:
  i) $A^1$ is not $CR^4$ where $R^4$ is H, Cl, F, Br, $NO_2$, or Me;
b) when $R^1$ is $-(L)_m Ar^1$, m is zero, and $Ar^1$ is phenyl, 4-OMe phenyl, 3,4-diOMe phenyl, or 4-Cl phenyl then:
  i) $A^3$ is not $CR^4$ where $R^4$ is Me when $R^2$ is H, when T is $CR^3$ where $R^3$ is H and when $A^1$ and $A^2$ are $CR^4$ where each $R^4$ is H;
  ii) $A^3$ is not $CR^4$ where $R^4$ is Br and $A^1$ is not $CR^4$ where $R^4$ is Me, when $R^2$ is H, when T is $CR^3$ where $R^3$ is H, and when $A^2$ is $CR^4$ where $R^4$ is H;
  iii) $A^2$ is not $CR^4$ where $R^4$ is Me, when $R^2$ is H, when T is $CR^3$ where $R^3$ is H and when $A^1$ and $A^3$ are each $CR^4$ where $R^4$ is H;
  iv) $A^1, A^2, A^3$ are not $CR^4$ where each $R^4$ is H, when T is $CR^3$ where $R^3$ is H and $R^2$ is Me;
  v) $A^1, A^2, A^3$ are not $CR^4$ where each $R^4$ is H, when T is $CR^3$ where $R^3$ is H and $R^2$ is H;
  vi) $A^2$ and $A^3$ are not $CR^4$ where both $R^4$ groups are taken together to form a fused benzo ring, when T is $CR^3$ where $R^3$ is H and when $A^1$ is $CR^4$ where $R^4$ is H;
c) when $R^1$ and $R^2$ are H, then:
  i) T is not $CR^3$ where $R^3$ is H, and $A^1, A^2$, and $A^3$ are not $CR^4$ where each $R^4$ is H;
  ii) $A^1$ is not $CR^4$ where $R^4$ is Cl, $NO_2$, or Me when T is $CR^3$ where $R^3$ is H and when $A^2$ and $A^3$ are $CR^4$ where each $R^4$ is H;
  iii) $A^2$ is not $CR^4$ where $R^4$ is Me, Et, OH, OEt, OMe, or Cl when T is $CR^3$ where $R^3$ is H and when $A^1$ and $A^3$ are $CR^4$ where each $R^4$ is H;
  iv) $A^2$ is not $CR^4$ where $R^4$ is Et, OH, OEt, OMe and $A^3$ is not $CR^4$ where $R^4$ is $NO_2$ when T is $CR^3$ where $R^3$ is H and when $A^1$ is $CR^4$ where $R^4$ is H;
  v) $A^2$ is not $CR^4$ where $R^4$ is Me, Et, OH, OEt, or OMe and $A^3$ is not $CR^4$ where $R^4$ is $NH_2$, $-N(CH_2)_2N(n-Pr)_2$, $-N(CH_2)_2N(Et)_2$, $-N(CH_2)_2NH_2$, $-N(CH_2)_4N(n-Pr)_2$, or $-N(CH_2)_4N(Et)_2$, when T is $CR^3$ where $R^3$ is H and when $A^1$ is $CR^4$ where $R^4$ is H;
  vi) $A^1$ and $A^2$ are not $CR^4$ where both $R^4$ groups are taken together to form a fused benzo or cyclohexyl ring, when T is $CR^3$ where $R^3$ is H and when $A^3$ is $CR^4$ where $R^4$ is H;
d) when $R^1$ is 3,6-dimethylbenzofuran-2-yl or benzofuran-2-yl and $R^2$ is H, then:
  i) $A^2$ is not $CR^4$ where $R^4$ is Me or H when T is $CR^3$ where $R^3$ is H and when $A^1$ and $A^3$ are $CR^4$ where each $R^4$ is H;
  ii) $A^1$ is not $CR^4$ where $R^4$ is Me when T is $CR^3$ where $R^3$ is H and when $A^2$ and $A^3$ are $CR^4$ where each $R^4$ is H;
e) when $R^1$ is Me and $R^2$ is H, then:
  i) $A^3$ is not $CR^4$ where $R^4$ is Me when T is $CR^3$ where $R^3$ is H and when $A^1$ and $A^2$ are $CR^4$ where each $R^4$ is H;
  ii) $A^1$ is not $CR^4$ where $R^4$ is Me when T is $CR^3$ where $R^3$ is H and when $A^2$ and $A^3$ are $CR^4$ where each $R^4$ is H;
  iii) T is not $CR^3$ where $R^3$ is OMe and $A^3$ is not $CR^4$ where $R^4$ is OMe and when $A^1$ and $A^2$ are $CR^4$ where each $R^4$ is H;
  iv) $A^1$ and $A^2$ are not $CR^4$ where $R^4$ is OMe when T is $CR^3$ where $R^3$ is H and when $A^3$ is $CR^4$ where $R^4$ is H;
  v) $A^2$ is not $CR^4$ where $R^4$ is OMe and $A^1$ is not $CR^4$ where $R^4$ is Me when T is $CR^3$ where $R^3$ is H and when $A^3$ is $CR^4$ where $R^4$ is H;
  vi) $A^3$ is not $CR^4$ where $R^4$ is Me and $A^2$ is not $CR^4$ where $R^4$ is OH when T is $CR^3$ where $R^3$ is H and when $A^1$ is $CR^4$ where $R^4$ is H;
  vii) T is not $CR^3$ where $R^3$ is H and $A^1, A^2$, and $A^3$ are not $CR^4$ where each $R^4$ is H;
  viii) $A^3$ is not $CR^4$ where $R^4$ is Me and when $A^2$ is not $CR^4$ where $R^4$ is OH when T is H and when $A^1$ is $CR^4$ where $R^4$ is H;
  ix) $A^2$ and $A^3$ are not $CR^4$ where both $R^4$ groups are taken together to form a fused benzo ring or a fused furanyl-2-carboxylic methyl ester, when T is $CR^3$ where $R^3$ is H and when $A^1$ is $CR^4$ where $R^4$ is H;
f) when $R^2$ is Me and $R^1$ is H, then:
  i) T is not $CR^3$ where $R^3$ is H and $A^1, A^2$, and $A^3$ are not $CR^4$ where each $R^4$ is H;
  ii) $A^1$ is not $CR^4$ where $R^4$ is Me or Cl when T is $CR^3$ where $R^3$ is H and when $A^2$ and $A^3$ are $CR^4$ where each $R^4$ is H;
  iii) $A^1$ and $A^3$ are not $CR^4$ where each $R^4$ is Cl when T is $CR^3$ where $R^3$ is H and when $A^2$ is $CR^4$ where $R^4$ is H;
  iv) $A^3$ is not $CR^4$ where $R^4$ is Me when T is $CR^3$ where $R^3$ is H and when $A^1$ and $A^2$ are $CR^4$ where each $R^4$ is H;
  v) $A^2$ is not $CR^4$ where $R^4$ is Me when T is $CR^3$ where $R^3$ is H and when $A^1$ and $A^3$ are $CR^4$ where each $R^4$ is H;
  vi) $A^3$ is not $CR^4$ where $R^4$ is Me when T is $CR^3$ where $R^3$ is H and when $A^1$ and $A^2$ are $CR^4$ where each $R^4$ is H;
g) when $R^1$ and $R^2$ are simultaneously Me, then:
  i) T is not $CR^3$ where $R^3$ is H and $A^1, A^2$, and $A^3$ are not $CR^4$ where each $R^4$ is H;
  ii) $A^1$ is not $CR^4$ where $R^4$ is Me, Cl, or $SO_3H$ when T is $CR^3$ where $R^3$ is H and when $A^2$ and $A^3$ are $CR^4$ where each $R^4$ is H;
  iii) $A^1$ and $A^3$ are not each $CR^4$ where $R^4$ is Me when T is $CR^3$ where $R^3$ is H and when $A^2$ is $CR^4$ where $R^4$ is H;
  iv) $A^3$ is not $CR^4$ where $R^4$ is Me when T is $CR^3$ where $R^3$ is H and when $A^1$ and $A^2$ are $CR^4$ where each $R^4$ is H;
  v) T is not $CR^3$ where $R^3$ is Me when $A^1, A^2$, and $A^3$ are $CR^4$ where each $R^4$ is H;
  vi) $A^2$ is not $CR^4$ where $R^4$ is Me when T is $CR^3$ where $R^3$ is Me and when $A^1$ and $A^2$ are $CR^4$ where each $R^4$ is H;
h) when T is $CR^3$ where $R^3$ is H and $A^1, A^2$, and $A^3$ are $CR^4$ where each $R^4$ is H, then:
  i) $R^1$ is not acetyl, propionyl, butyryl or sec-butyryl;
j) when $R^1$ is Me or Et and $R^2$ is acetyl or propionyl, then:
  i) $A^1$ and $A^3$ are not $CR^4$ where $R^4$ is Me when T is $CR^3$ where $R^3$ is H and when $A^2$ is $CR^4$ where $R^4$ is H;
  ii) $A^1$ is not $CR^4$ where $R^4$ is Me when T is $CR^3$ where $R^3$ is H and when $A^2$ and $A^3$ are $CR^4$ where each $R^4$ is H;
  iii) $A^1$ and $A^2$ are not $CR^4$ where both $R^4$ groups are taken together to form a fused benzo ring, when T is $CR^3$ where $R^3$ is H and when $A^3$ is $CR^4$ where $R^4$ is H;
  iv) $A^2$ is not $CR^4$ where $R^4$ is Me when T is $CR^3$ where $R^3$ is H and when $A^1$ and $A^3$ are $CR^4$ where each $R^4$ is H;
k) when $R^2$ is H, SH, OH, $-OR$, $N(R)_2$, and T is $CR^3$ wherein $R^3$ is H, an optionally substituted $C_{1-6}$ aliphatic group, OH, $NH_2$, SH, OR, halogen or $N(R)_2$, and $A^1, A^2$, and $A^3$ are $CR^4$ where $R^4$ is hydrogen, halogen or $-(L)_m R$ wherein m is 1, L is $-S-$, $-O-$, $-N(R)-$, and R is H or an optionally substituted $C_{1-6}$ aliphatic group, then $R^1$ is not:
  i) $-(L)_m R$ wherein m is 0 and R is an optionally substituted $C_{1-6}$ aliphatic group; or
  ii) $-(L)_m R$ wherein m is 1 and L is $-S-$, $-O-$, $-N(R)-$, and R is an optionally substituted $C_{1-6}$ aliphatic group;

l) when $A^2$ and $A^3$ are $CR^4$ where both $R^4$ groups are taken together to form a fused benzo ring, and when T is $CR^3$ where $R^3$ is H, then $R^1$ is not:
  i) p-chlorostyryl, styryl, p-methylstyryl, or p-methoxystyryl;

and also provided that the following compounds are excluded:
6-Chloro-2-(2,3-dihydro-benzo[1,4]dioxin-6-yl)-chromen-4-one oxime,
3-Acetyl-5-chloro-2,6-dimethyl-chromen-4-one oxime,
2,3-Dihydro-1,5-dioxa-cyclopenta[b]naphthalene-8-one oxime,
4,9-Dimethoxy-7-methyl-furo[3,2-g]chromen-5-one oxime,
4,7,9-Trimethyl-furo[3,2-g]chromen-5-one oxime,
5,6,7,8-Tetrafluoro-4-hydroxyimino-2-methyl-4H-chromene-3-carboxylic acid ethyl ester,
Nicotinic acid 5-hydroxyimino-9-methoxy-7-methyl-5H-furo[3,2,g]chromen-4-yl ester,
Benzoic acid 5-hydroxyimino-9-methoxy-7-methyl-5H-furo[3,2,g]chromen-4-yl ester,
4-(2-Diethylamino-ethoxy)-9-methoxy-7-methyl-furo[3,2,g]chromen-5-one oxime,
4-Benzyloxy-9-methoxy-7-methyl-furo[3,2,g]chromen-5-one oxime,
Acetic acid 5-hydroxyimino-9-methoxy-7-methyl-5H-furo[3,2,g]chromen-4-yl ester,
4-Hydroxy-9-methoxy-7-methyl-furo[3,2,g]chromen-5-one oxime,
2-(3,4-Dihydroxy-phenyl)-5,7-dihydroxy-chromen-4-one oxime,
6-[4-(1-Hydroxyimino-ethyl)-phenoxy]-5,7-dimethoxy-2-(4-methoxy-phenyl)-chromen-4-one oxime,
8-(4-Acetyl-phenoxy)-5,7-dihydroxy-2-(4-hydroxy-phenyl)-chromen-4-one oxime,
6-(4-Acetyl-phenoxy)-5,7-dihydroxy-2-(4-hydroxy-phenyl)-chromen-4-one oxime,
2-(2,6-Dimethoxy-phenyl)-5,6-dimethoxy-chromen-4-one oxime,
2-(2,4-Dimethoxy-phenyl)-7-methoxy-chromen-4-one oxime,
6-Chloro-3-ethyl-2-methyl-chromen-4-one oxime,
(4-Hydroxyimino-4H-chromen-3-yl)-acetic acid,
3-(1-Hydroxyimino-ethyl)-2,6-dimethyl-chromen-4-one oxime,
Acetic acid 3,7-diacetoxy2-(4-acetoxy-phenyl)-4-hydroxyimino-4H-chromen-5-yl ester,
2-(3,4-dimethoxy-phenyl)-3,5,7-trimethoxy-chromen-4-one oxime,
3,5,7-trimethoxy-2-(4-methoxy-phenyl)-chromen-4-one oxime,
8-[4-(1-hydroxyimino-ethyl)-phenoxy]-5,7-dimethoxy-2-(4-methoxy-phenyl)chromen-4-one oxime,
8-[5-(1-hydroxyimino-ethyl)-2-methoxy-phenyl]-5,7-dimethoxy-2-(4-methoxy-phenyl)chromen-4-one oxime,
4-hydroxyimino-7-methoxy-4H-chromen-3-yl)-acetic acid.

II. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —$R^o$; —$OR^o$; —$SR^o$; 1,2-methylenedioxy; 1,2-ethylenedioxy; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —$N(R^o)_2$; —$NR^oC(O)R^o$; —$NR^oC(S)R^o$; —$NR^oC(O)N(R^o)_2$; —$NR^oC(S)N(R^o)_2$; —$NR^oCO_2R^o$; —$NR^oNR^oC(O)R^o$; —$NR^oNR^oC(O)N(R^o)_2$; —$NR^oNR^oCO_2R^o$; —$C(O)C(O)R^o$; —$C(O)CH_2C(O)R^o$; —$CO_2R^o$; —$C(O)R^o$; —$C(S)R^o$; —$C(O)N(R^o)_2$; —$C(S)N(R^o)_2$; —$OC(O)N(R^o)_2$; —$OC(O)R^o$; —$C(O)N(OR^o)R^o$; —$C(NOR^o)R^o$; —$S(O)_2R^o$; —$S(O)_3R^o$; —$SO_2N(R^o)_2$; —$S(O)R^o$; —$NR^oSO_2N(R^o)_2$; —$NR^oSO_2R^o$; —$N(OR^o)R^o$; —C(=NH)—$N(R^o)_2$; or —$(CH_2)_{0-2}NHC(O)R^o$ wherein each independent occurrence of $R^o$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of $R^o$ are selected from $NH_2$, $NH(C_{1-4}$aliphatic), $N(C_{1-4}$aliphatic)$_2$, halogen, $C_{1-4}$aliphatic, OH, $O(C_{1-4}$aliphatic), $NO_2$, CN, $CO_2H$, $CO_2(C_{1-4}$aliphatic), $O(haloC_{1-4}$ aliphatic), or $haloC_{1-4}$aliphatic, wherein each of the foregoing $C_{1-4}$ aliphatic groups of $R^o$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from —$R^+$, —$N(R^+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —C(=S)$N(R^+)_2$, —C(=NH)—$N(R^+)_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of $R^o$ (or $R^+$, or any other variable similarly defined herein), are taken together together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of R° (or R+, or any other variable similarly defined herein) that are bound to different atoms and are taken together with both of those atoms to form a ring, for example where a phenyl group is substituted with two occurrences of OR°

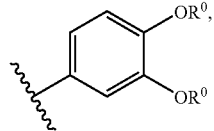

these two occurrences of R° are taken together with the oxygen atoms to which they are bound to form a fused 6-membered oxygen containing ring:

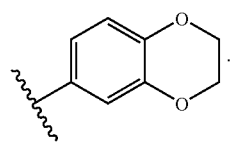

It will be appreciated that a variety of other rings can be formed when two independent occurrences of R° (or R+, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

III. Description of Certain Exemplary Compounds

According to one embodiment, $R^1$ is $-(L)_m Ar$, $-(L)_m R$, or $-(L)_m Cy^1$. In another embodiment, $R^1$ is $-(L)_m Ar^1$ and compounds have the general formula I:

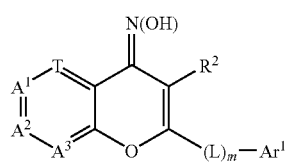

I

In another embodiment, $R^1$ is $-(L)_m Ar^1$ and $Ar^1$ is selected from one of the following groups:

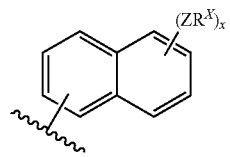

1-1

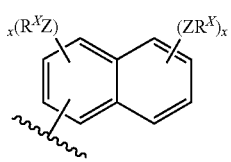

1-2

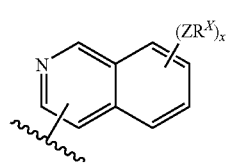

1-3

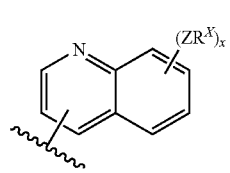

1-4

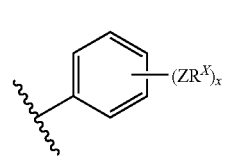

1-5

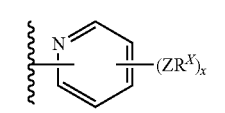

1-6

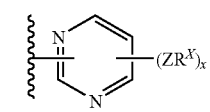

1-7

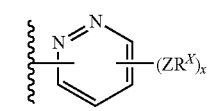

1-8

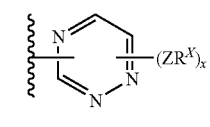

1-9

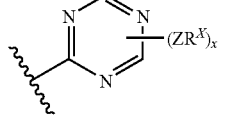

1-10

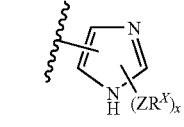

1-11

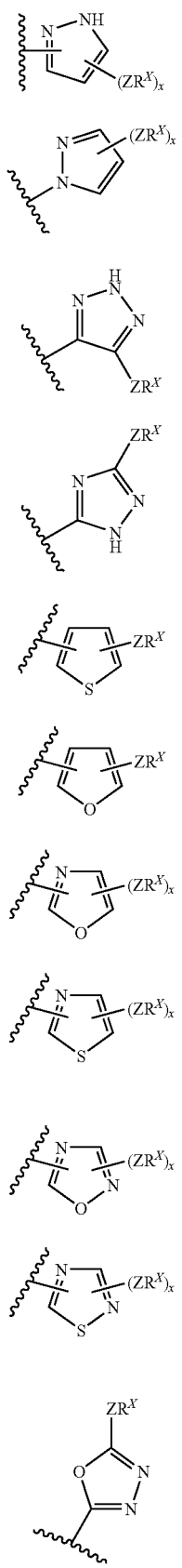
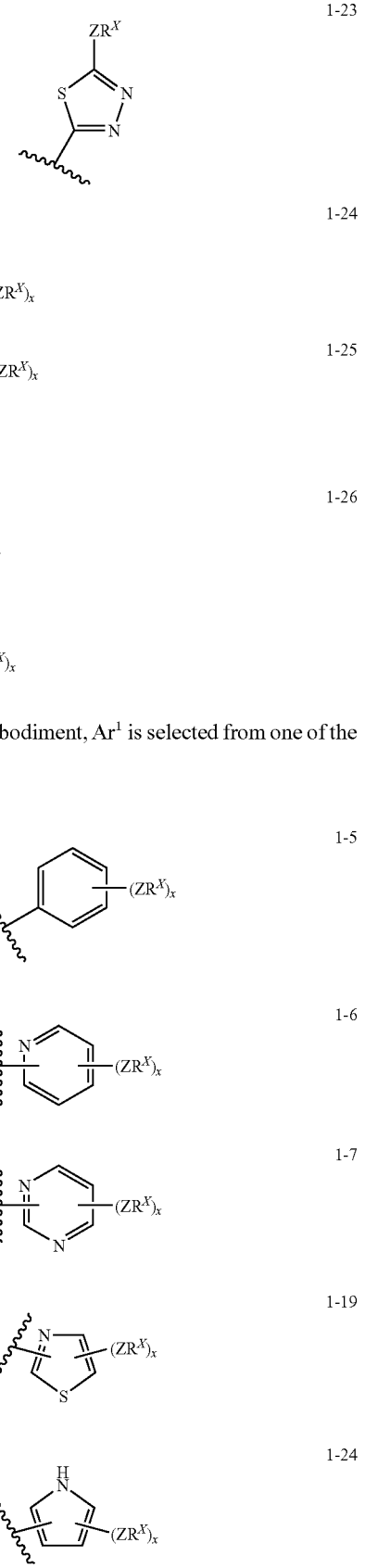
In yet another embodiment, Ar¹ is selected from one of the following groups:

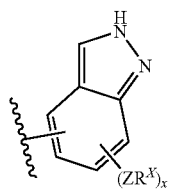

According to another embodiment R¹ is -(L)$_m$-Ar¹, m is 1 and compounds have the formula IA-1:

IA-1

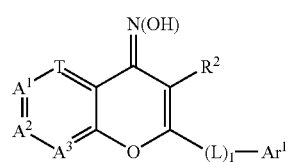

In another embodiment Ar¹ is phenyl with 0-5 occurrences of ZR$^X$ and compounds have the formula IA-1-5:

IA-1-5

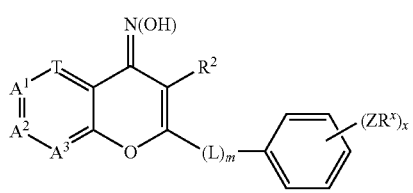

According to another embodiment R¹ is -(L)$_m$-Cy¹, and compounds have the formula IA-2:

IA-2

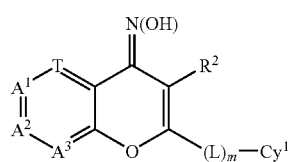

In another embodiment, Cy¹ is selected from one of the following groups:

2-1

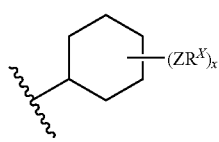

2-2

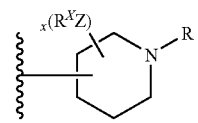

2-3

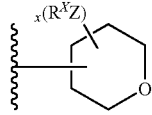

2-4

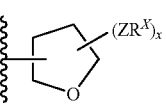

2-5

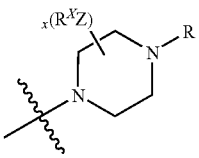

2-6

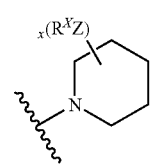

2-7

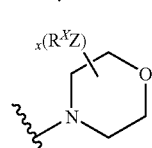

2-8

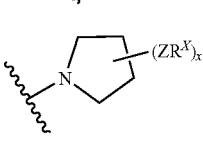

2-9

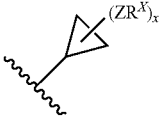

2-10

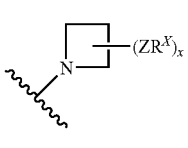

2-11

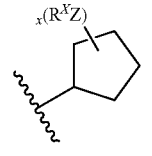

2-12

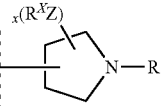

According to another embodiment where R¹ is -(L)$_m$Ar¹ or -(L)$_m$Cy¹, L is an optionally substituted C$_{1-6}$ straight or branched alkylidene chain wherein one methylene unit of L is optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O).

In another embodiment, L is an optionally substituted $C_{1-6}$ straight or branched alkylidene chain wherein one methylene unit of L is optionally replaced by O, NR, NRCO, CO, CONR, $SO_2NR$, $NRSO_2$.

According to another embodiment, $R^1$ is -$(L)_m R$ and L is an optionally substituted $C_{1-6}$ straight or branched alkylidene chain wherein one methylene unit of L is optionally replaced by O, NR, NRCO, NRCONR, $NRCO_2$, CO, $CO_2$, CONR, OC(O)NR, $SO_2$, $SO_2NR$, $NRSO_2$, $NRSO_2NR$, and R is an optionally substituted $C_{1-6}$ aliphatic group.

In another embodiment, $R^2$ is hydrogen, CN, —OR, —$CO_2R$, —OC(O)R, —C(O)R, —C(O)N(R)$_2$, —N(R)$_2$, —N(R)C(O)R, or an optionally substituted $C_{1-6}$ aliphatic group.

In yet another embodiment, $R^2$ is hydrogen or an optionally substituted $C_{1-6}$ aliphatic group. In another embodiment, $R^2$ is hydrogen, methyl, ethyl, n-propyl, isopropyl, or cyclopropyl.

In yet another embodiment, $R^2$ is hydrogen and compounds have the formula IB:

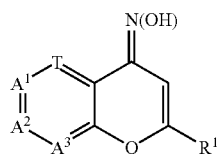

IB

In another embodiment, T is $CR^3$ and $R^3$ is hydrogen, halogen, CN, or an optionally substituted $C_{1-6}$ aliphatic group. In another embodiment, $R^3$ is hydrogen, halogen, $CF_3$, methyl, ethyl, n-propyl, isopropyl, or cyclopropyl. In yet another embodiment, $R^3$ is hydrogen or halogen.

According to another embodiment, T is $CR^3$, $R^3$ is hydrogen and compounds have the formula IC:

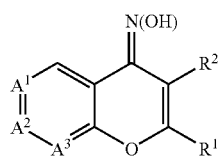

IC

In another embodiment, $A^1$ is $CR^4$ and $R^4$ is halogen, CN, -$(L)_m R$, -$(L)_m Ar^1$, or -$(L)_m Cy^1$. In another embodiment, when $A^1$ is $CR^4$ and $R^4$ is -$(L)_m R$, -$(L)_m Ar^1$, or -$(L)_m Cy^1$, wherein $Ar^1$ and $Cy^1$ groups are as described above, L is an optionally substituted $C_{1-6}$ straight or branched alkylidene chain wherein one methylene unit of L is optionally replaced by O, NR, NRCO, NRCONR, $NRCO_2$, CO, $CO_2$, CONR, OC(O)NR, $SO_2$, $SO_2NR$, $NRSO_2$, $NRSO_2NR$, C(O)C(O), or C(O)$CH_2$C(O).

According to yet another embodiment, $A^1$ is $CR^4$ and $R^4$ is halogen, CN, or R.

In other embodiments, $A^1$ is $CR^4$, $R^4$ is -$(L)_m R$, and compounds have the formula ID-1:

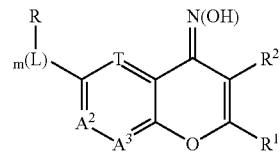

ID-1

According to still another embodiment, $A^1$ is $CR^4$, $R^4$ is -$(L)_m Ar^1$, and compounds have the formula ID-2:

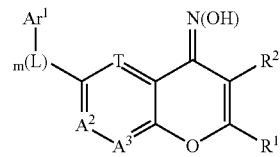

ID-2

In yet another embodiment, $A^1$ is $CR^4$, $R^4$ is -$(L)_m Cy^1$, and compounds have the formula ID-3:

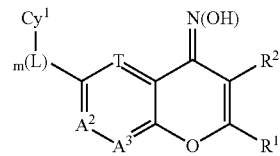

ID-3

According to another embodiment, $A^2$ is $CR^4$ and $R^4$ is halogen, CN, -$(L)_m R$, -$(L)_m Ar^1$, or -$(L)_m Cy^1$. In another embodiment, $A^2$ is $CR^4$ and $R^4$ is halogen or R. In yet another embodiment, L is an optionally substituted $C_{1-6}$ straight or branched alkylidene chain wherein one methylene unit of L is optionally replaced by O, NR, NRCO, NRCONR, $NRCO_2$, CO, $CO_2$, CONR, OC(O)NR, $SO_2$, $SO_2NR$, $NRSO_2$, $NRSO_2NR$, C(O)C(O), or C(O)$CH_2$C(O). In certain other embodiments, $A^2$ is $CR^4$ and $R^4$ is -$(L)_m R$, wherein L is —O— or —N(R)—.

According to another embodiment, $A^2$ is $CR^4$, $R^4$ is -$(L)_m R$, and compounds have the formula IE-1:

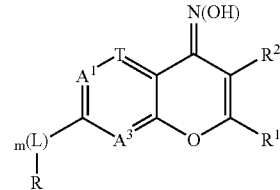

IE-1

In another embodiment, $A^2$ is $CR^4$, $R^4$ is -$(L)_m Ar^1$, and compounds have the formula IE-2:

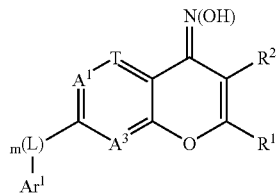

IE-2

In a yet another embodiment, $A^2$ is $CR^4$, $R^4$ is -(L)$_m$Ar$^1$, m is 0 and Ar$^1$ is 1-5, 1-6, 1-11, 1-12, 1-13, 1-19, 1-24, or 1-25.

In still another embodiment, $A^2$ is $CR^4$, $R^4$ is -(L)$_m$Cy$^1$, and compounds have the formula IE-3:

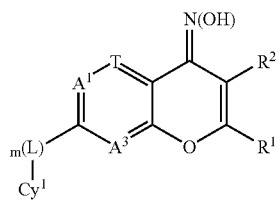

IE-3

In another embodiment, $A^2$ is $CR^4$, $R^4$ is -(L)$_m$Cy$^1$, m is 0 and Cy$^1$ is 2-2, 2-5, 2-6, 2-7, 2-8, or 2-12.

According to another embodiment, $A^3$ is $CR^4$ and $R^4$ is halogen, CN, -(L)$_m$R, -(L)$_m$Ar$^1$, or -(L)$_m$Cy$^1$. In another embodiment, $A^3$ is $CR^4$ and $R^4$ is halogen or R. In another embodiment L is an optionally substituted $C_{1-6}$ straight or branched alkylidene chain wherein one methylene unit of L is optionally replaced by O, NR, NRCO, NRCONR, NRCO$_2$, CO, CO$_2$, CONR, OC(O)NR, SO$_2$, SO$_2$NR, NRSO$_2$, NRSO$_2$NR, C(O)C(O), or C(O)CH$_2$C(O). More preferably, $A^3$ is $CR^4$ and $R^4$ is -(L)$_m$R, wherein L is —O— or —N(R)—.

In yet another embodiment, $A^3$ is $CR^4$, $R^4$ is -(L)$_m$R, and compounds have the formula IF-1:

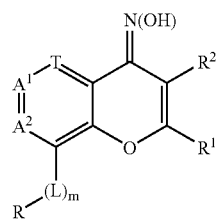

IF-1

In yet another embodiment, $A^3$ is $CR^4$, $R^4$ is -(L)$_m$Ar$^1$, and compounds have the formula IF-2:

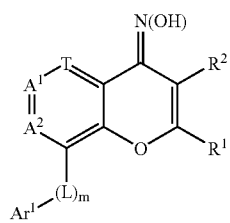

IF-2

In another embodiment, $A^3$ is $CR^4$, $R^4$ is -(L)$_m$Ar$^1$, m is 0 and Ar$^1$ is 1-5, 1-6, 1-11, 1-12, 1-13, 1-19, 1-24, or 1-25.

In still another embodiment, $A^3$ is $CR^4$, $R^4$ is -(L)$_m$Cy$^1$, and compounds have the formula IF-3:

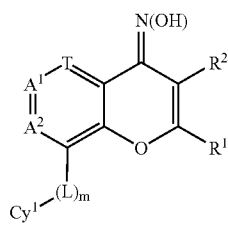

IF-3

In another embodiment, $A^3$ is $CR^4$, $R^4$ is -(L)$_m$Cy$^1$, m is 0 and Cy$^1$ is 2-2, 2-5, 2-6, 2-7, 2-8, or 2-12.

In yet another embodiment, T is $CR^3$, $A^1$, $A^2$ and $A^3$ are each $CR^4$ and compounds have the formula IG-1:

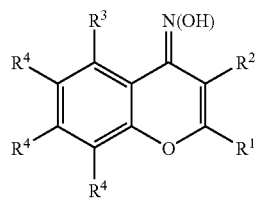

IG-1

According to another embodiment for compounds of formula I, x is 0-5, and Ar$^1$ and Cy$^1$ are independently substituted with 0-5 occurrences of ZR$^X$. Preferably, ZR$^X$ is independently halogen, NO$_2$, CN, or an optionally substituted group selected from $C_{1-4}$ alkyl, aryl, aralkyl, —N(R')$_2$, —CH$_2$N(R')$_2$, —OR', —CH$_2$OR', —SR', —CH$_2$SR', —COOR', or —S(O)$_2$N(R')$_2$. In another embodiment, ZR$^X$ groups are shown below in Table 1.

Representative examples of compounds of formula I are set forth below in Table 1.

TABLE 1

Examples of Compounds of Formula I:

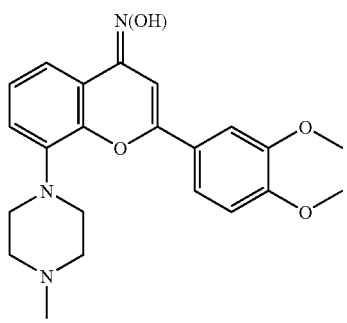

I-1

TABLE 1-continued
Examples of Compounds of Formula I:
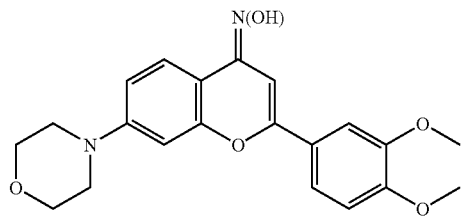
I-2
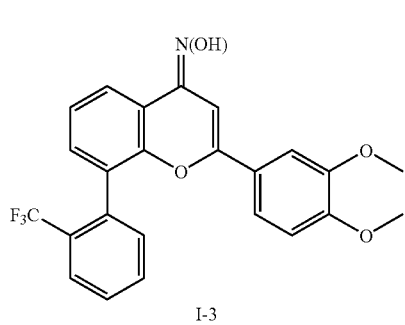
I-3
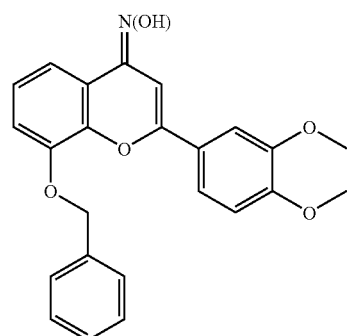
I-4
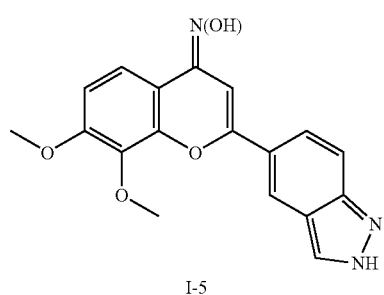
I-5
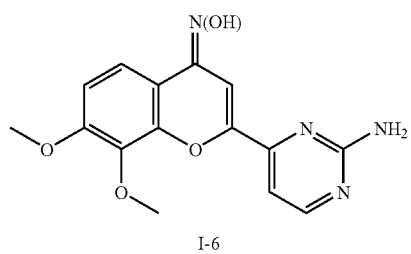
I-6
TABLE 1-continued
Examples of Compounds of Formula I:
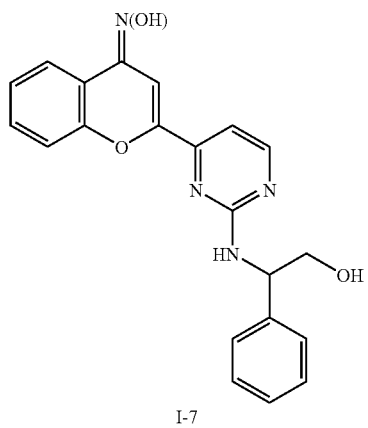
I-7
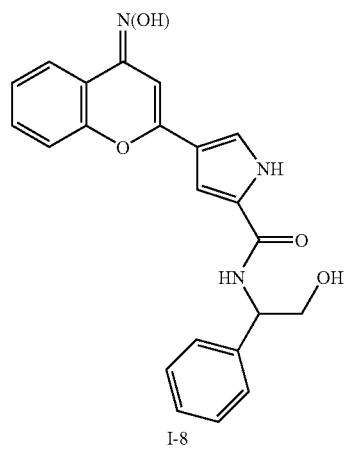
I-8
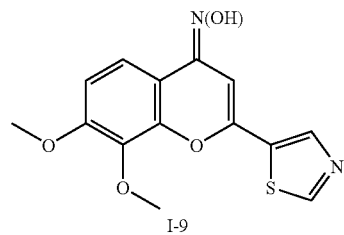
I-9
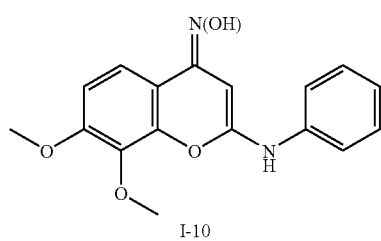
I-10

TABLE 1-continued
Examples of Compounds of Formula I:
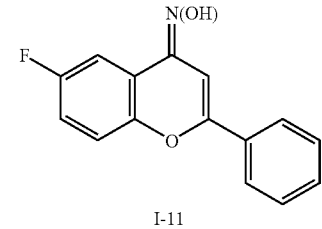
I-11
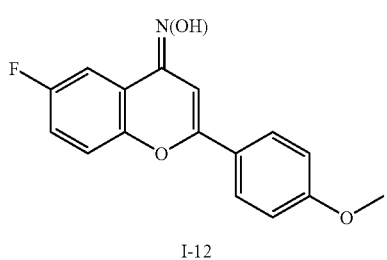
I-12
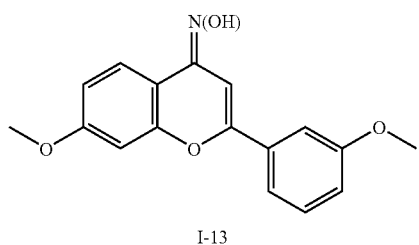
I-13
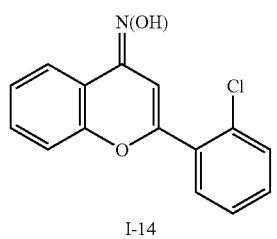
I-14
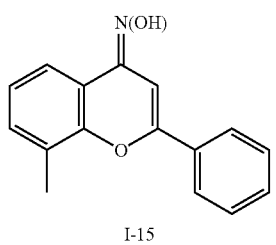
I-15
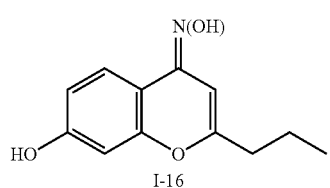
I-16
TABLE 1-continued
Examples of Compounds of Formula I:
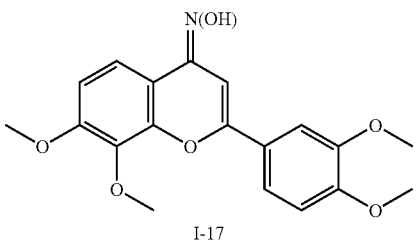
I-17
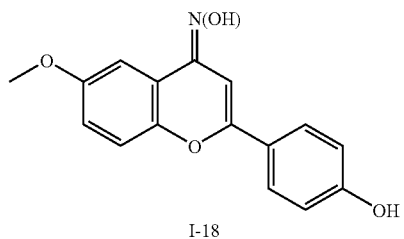
I-18
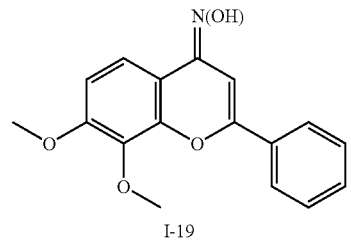
I-19
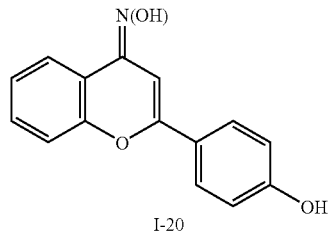
I-20
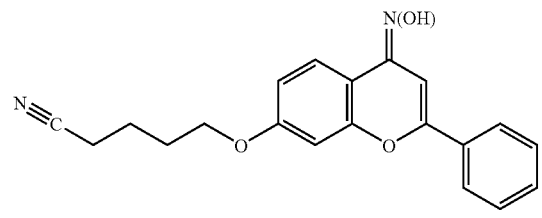
I-21
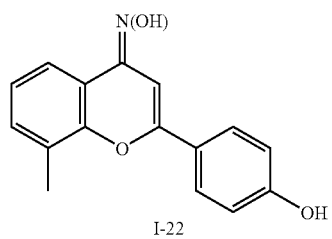
I-22

TABLE 1-continued
Examples of Compounds of Formula I:
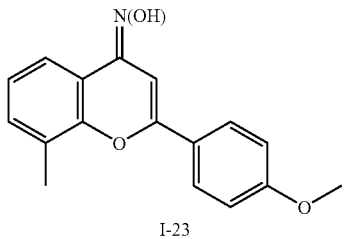
I-23
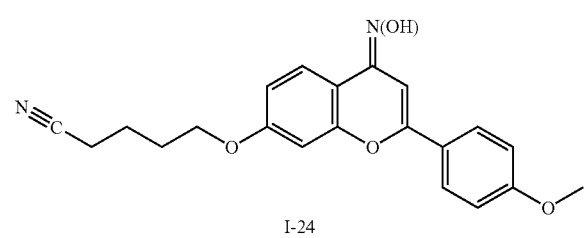
I-24
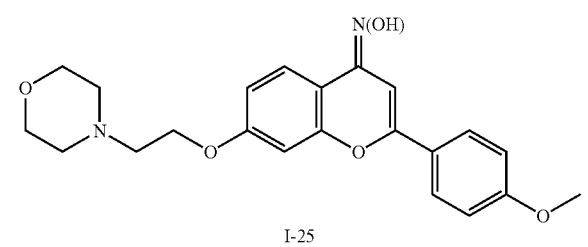
I-25
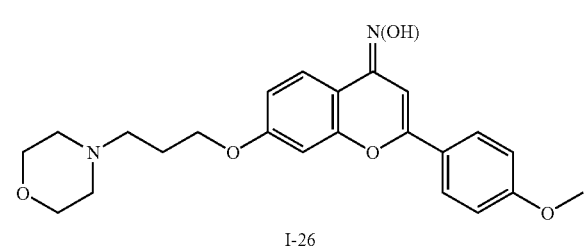
I-26
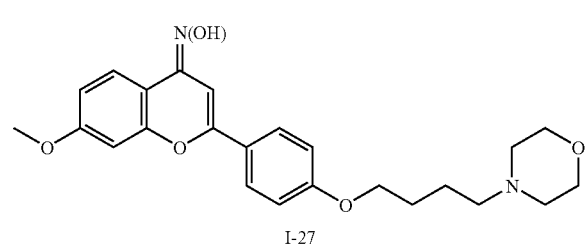
I-27
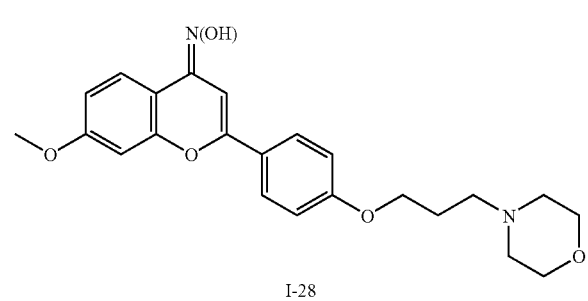
I-28
TABLE 1-continued
Examples of Compounds of Formula I:
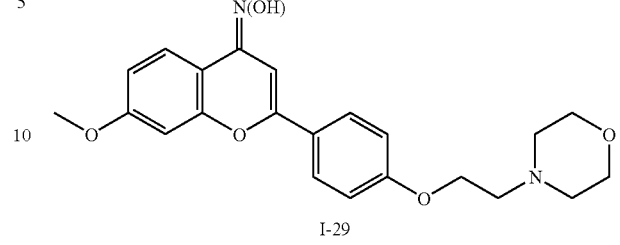
I-29
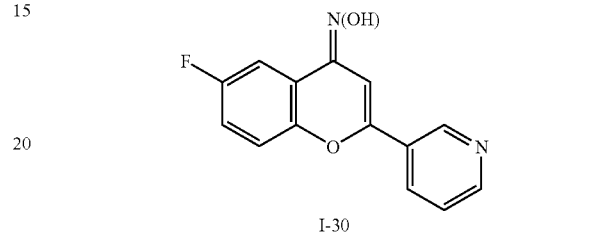
I-30
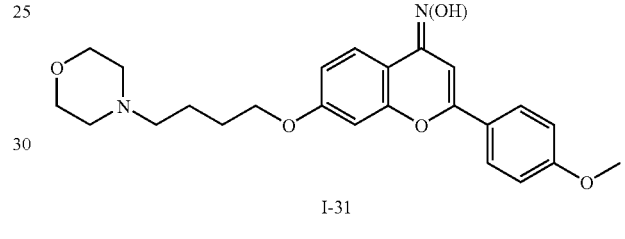
I-31
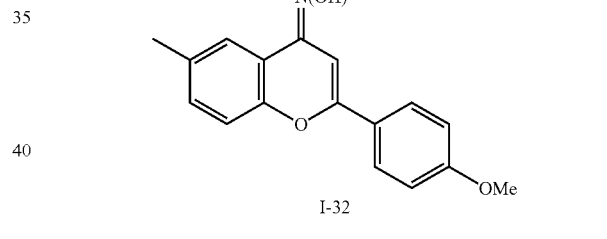
I-32
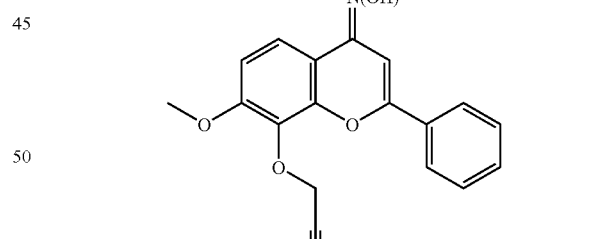
I-33
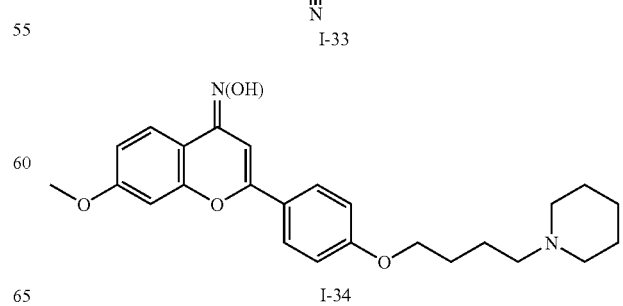
I-34

TABLE 1-continued

Examples of Compounds of Formula I:

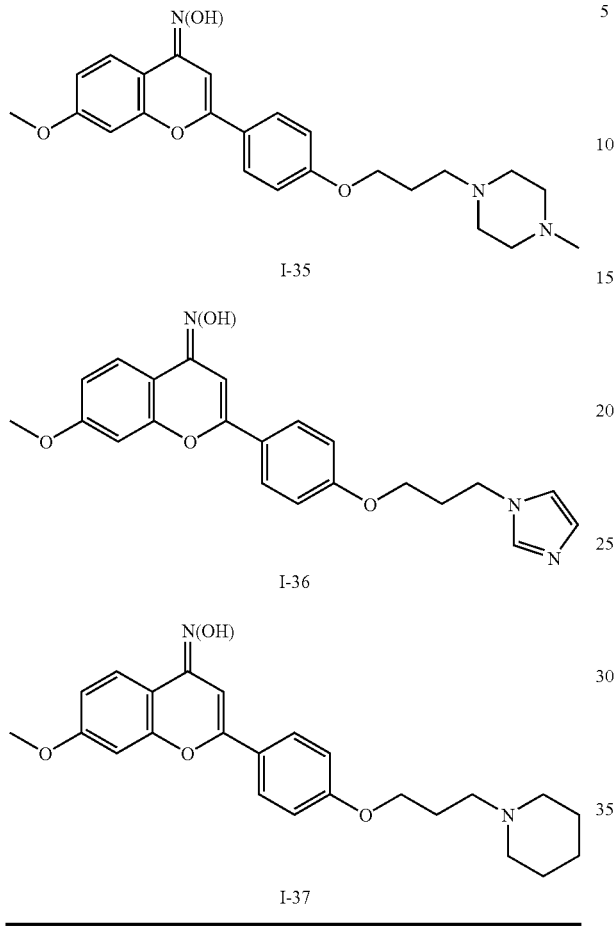

I-35

I-36

I-37

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

IV. General Synthetic Methodology

The compounds of this invention may be prepared in general by methods known to those skilled in the art for analogous compounds. Schemes 1-4 below illustrate synthetic routes to the compounds of the present invention. Other equivalent schemes, which will be readily apparent to the ordinary skilled organic chemist, may alternatively be used to synthesize various portions of the molecule as illustrated by the general scheme below, and the preparative examples that follow.

Scheme 1:

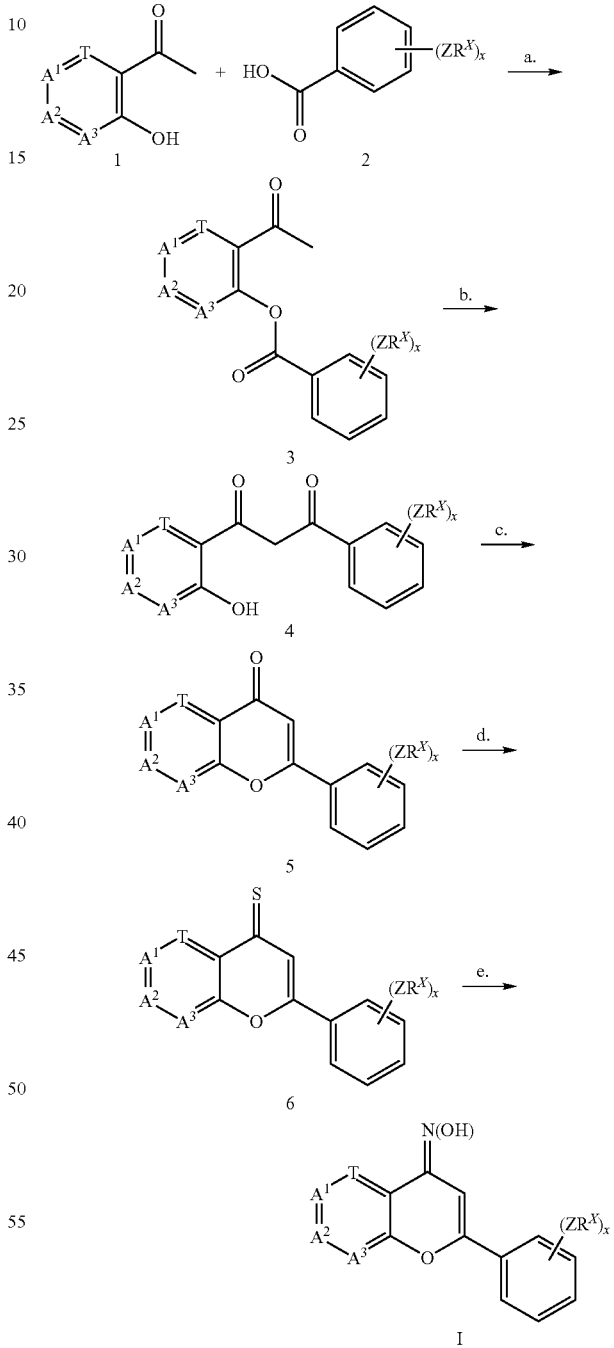

Reagents: (a) EDCI, HOBt, THF; (b) NaH, DMSO; (c) HOAc, HCl; (d) $P_2S_5$ or Lawesson's reagent; (e) $NH_2OH$, Pyridine, 90°.

Scheme 1 above shows a general method for preparing compounds of formula I. For example, intermediate ester 3 may be prepared according to the method of Hassner, A. et al., *Tett. Lett.* 1978, 26, 4475-4478, wherein hydroxy-2-acetylarene 1 is reacted with aryl acid 2 to provide ester 3. Rearrangement followed by acidic cyclization according to the method of Hamada, M. et al., *Synthesis* 1984, 1076-1078, provided intermediate flavone 5. Flavone 5 was converted to thioflavone 6 according to the method of either Ollis, W. et al., *J. Chem. Soc.* 1952, 1303-1309 or Lawesson, S. O. et al., *Bull. Soc. Chim. Belg.* 1978, 87, 223-228. Thioflavone 5 was converted into flavone oxime I using the protocol described by Ollis, W. et al., *J. Chem. Soc.* 1952, 1303-1309.

Scheme 2:

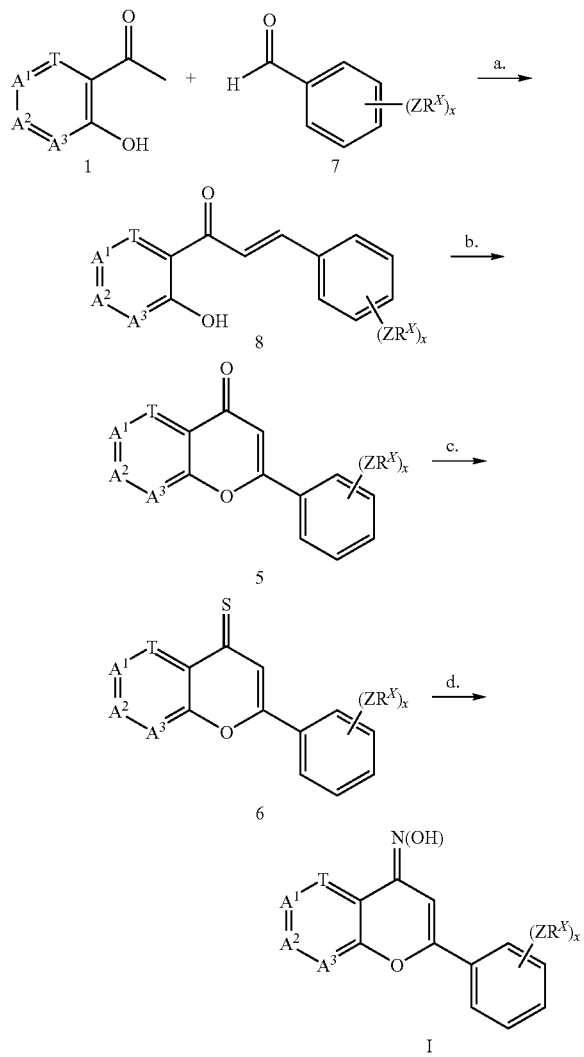

Reagents: (a) NaOH, EtOH; (b) $I_2$ cat., DMSO; (c) $P_2S_5$ or Lawesson's reagent; (d) $NH_2OH$, Pyridine, 90°.

Scheme 2 above shows an alternate general route for the preparation of compounds of formula I. Condensation of hydroxy-2-acetylarene 1 with aryl aldehyde 7 according to the procedure of Geissman, T. A. et al., *J. Amer. Chem. Soc.* 1954, 3507-3511, afforded 2'-hydroxychalcone 8 which was converted into the corresponding flavone 5 using the procedure developed by Doshi, A. G. et al., *Indian J. Chem.* 1986, 25B, 759. Flavone 5 was converted to thioflavone 6 and then to flavone oxime I according to the methods described above in Scheme 1.

Scheme 3:

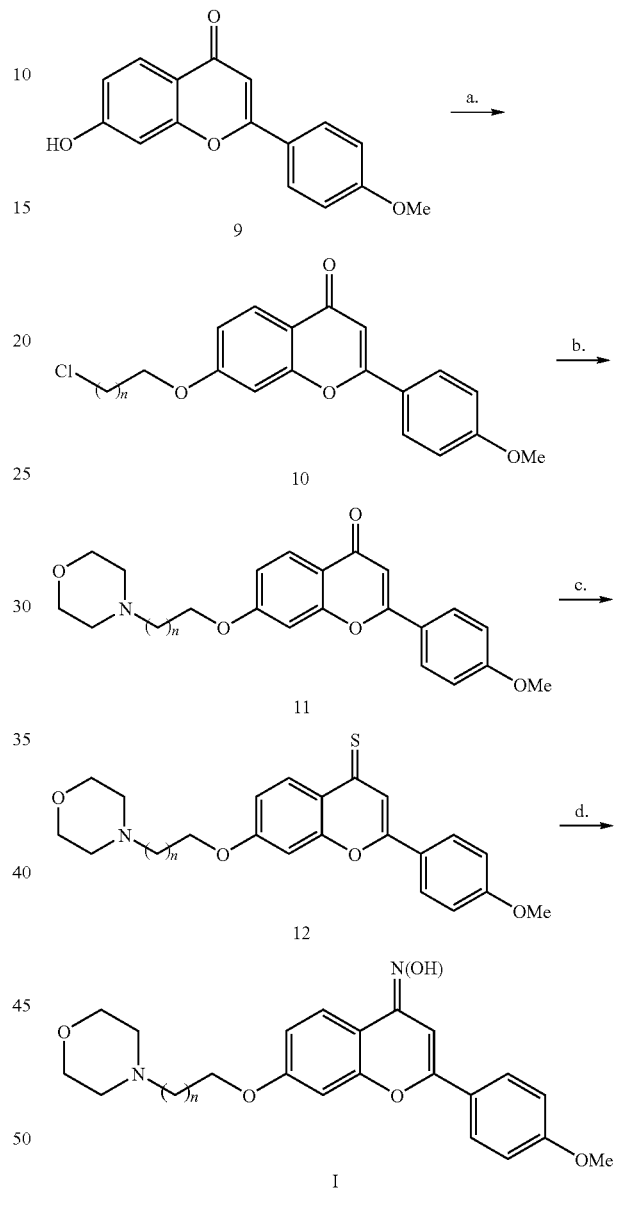

Reagens: (a) $BrCH_2(CH_2)_nCl$, $K_2CO_3$, acetone, reflux; (b) morpholine, $K_2CO_3$, NaI, 2-butanone; (c) Lawesson's reagent, toluene, reflux; (d) $NH_2OH$, Pyridine, 110°.

Scheme 3 above shows a general route for the preparation of compounds of formula I, specifically compounds I-25, I-26, and I-31. Commercially available hydroxy flavone 9 was alkylated in refluxing acetone to give chloride 10 which was subsequently morpholine to give ether 11. Conversion of the flavone 11 to thioflavone 12 and then to flavone oxime I was accomplished generally according to the methods listed above in Scheme 1.

Scheme 4:

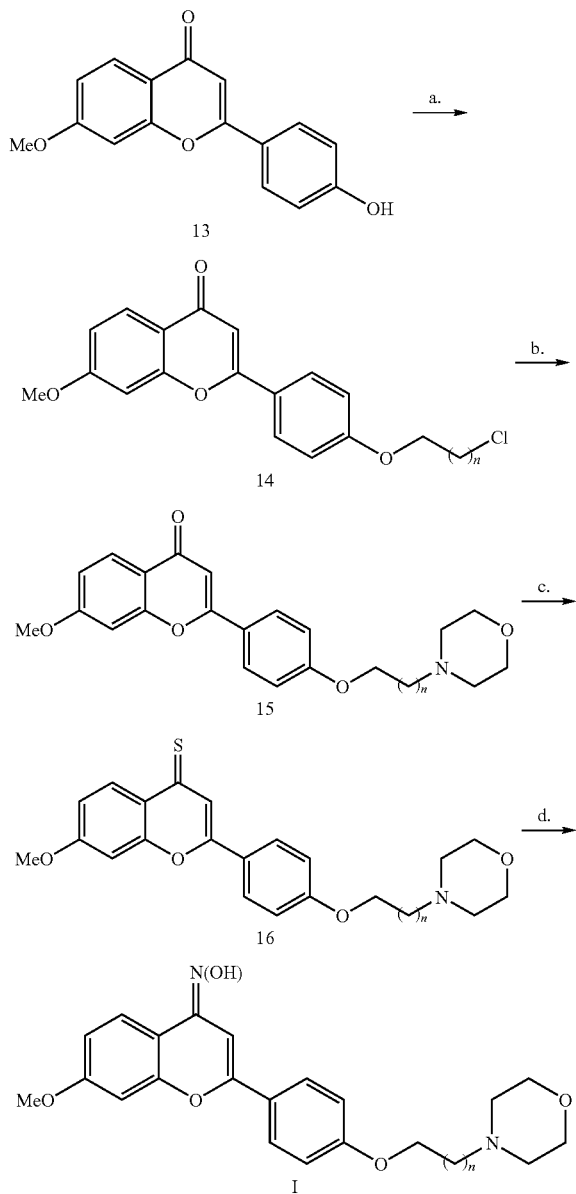

Reagents: (a) BrCH$_2$(CH$_2$)$_n$Cl, K$_2$CO$_3$, acetone, reflux; (b) morpholine, K$_2$CO$_3$, NaI, 2-butanone; (c) Lawesson's reagent, toluene, reflux; (d) NH$_2$OH, Pyridine, 110°.

Scheme 4 above shows a general route for the preparation of compounds of formula I, specifically compounds I-27, I-28, I-29, I-34, I-35, and I-37. Commercially available hydroxy flavone 13 was alkylated in refluxing acetone to give chloride 14 which was subsequently displaced with morpholine to give ether 15. Conversion of the flavone 15 to thioflavone 16 and then to flavone oxime I was accomplished generally according to the methods listed above for Scheme 1.

Although certain exemplary embodiments are depicted and described above and herein, it will be appreciated that a compounds of the invention can be prepared according to the methods described generally above using appropriate starting materials by methods generally available to one of ordinary skill in the art.

V. Uses, Formulation, and Administration

Pharmaceutically Acceptable Compositions

As discussed above, the present invention provides compounds that are inhibitors of protein kinases, and thus the present compounds are useful for the treatment of diseases, disorders, and conditions including, but not limited to cancer, a proliferative disorder, a cardiac disorder, a neurodegenerative disorder, an autoimmune disorder, a condition associated with organ transplant, an inflammatory disorder, an immunologically mediated disorder, a viral disease, or a bone disorder. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a CDK-2, cMET, FLT-3, JAK-3, GSK-3, IRAK-4, SYK, p70S6K, TAK-1, and ZAP-70 kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of cancer, a proliferative disorder, a cardiac disorder, a neurodegenerative disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for cancer, a proliferative disorder, a cardiac disorder, a neurodegenerative disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for treating or lessening the severity of cancer, a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of CDK-2, cMET, FLT-3, JAK-3, GSK-3, IRAK-4, SYK, p70S6K, TAK-1, and ZAP-70 kinase, and thus, without wishing to be bound by any particular theory, the compounds and compositions are particularly useful for treating or lessening the severity of a disease, condition, or disorder where activation of one or more of CDK-2, cMET, FLT-3, JAK-3, GSK-3, IRAK-4, SYK, p70S6K, TAK-1, and ZAP-70 is implicated in the disease, condition, or disorder. When activation of CDK-2, cMET, FLT-3, JAK-3, GSK-3, IRAK-4, SYK, p70S6K, TAK-1, and ZAP-70 is implicated in a particular disease, condition, or disorder, the disease, condition, or disorder may also be referred to as "CDK-2-, cMET-, FLT-3-, JAK-3-, GSK-3-, IRAK-4-, SYK-, p70S6K-, TAK-1-, and ZAP-70-mediated disease" or disease symptom. Accordingly, in another aspect, the present invention provides a method for treating or lessening the severity of a disease, condition, or disorder where activation or one or more of CDK-2, cMET, FLT-3, JAK-3, GSK-3, IRAK-4, SYK, p70S6K, TAK-1, and ZAP-70 is implicated in the disease state.

The activity of a compound utilized in this invention as an inhibitor of CDK-2, cMET, FLT-3, JAK-3, GSK-3, IRAK-4, SYK, p70S6K, TAK-1, and ZAP-70 kinase, may be assayed in vitro, in vivo or in a cell line. In vitro assays include assays that determine inhibition of either the phosphorylation activity or ATPase activity of activated CDK-2, cMET, FLT-3, JAK-3, GSK-3, IRAK-4, SYK, p70S6K, TAK-1, and ZAP-70 kinase. Alternate in vitro assays quantitate the ability of the inhibitor to bind to CDK-2, cMET, FLT-3, JAK-3, GSK-3, IRAK-4, SYK, p70S6K, TAK-1, or ZAP-70 kinase. Inhibitor binding may be measured by radiolabelling the inhibitor prior to binding, isolating the inhibitor/CDK-2, cMET, FLT-3, JAK-3, GSK-3, IRAK-4, SYK, p70S6K, TAK-1, or ZAP-70 kinase complex and determining the amount of radiolabel bound. Alternatively, inhibitor binding may be determined by running a competition experiment where new inhibitors are incubated with CDK-2, cMET, FLT-3, JAK-3, GSK-3, IRAK-4, SYK, p70S6K, TAK-1, or ZAP-70, bound to known radioligands.

The term "measurably inhibit", as used herein means a measurable change in CDK-2, cMET, FLT-3, JAK-3, GSK-3, IRAK-4, SYK, p70S6K, TAK-1, or ZAP-70 activity between a sample comprising said composition and a CDK-2, cMET, FLT-3, JAK-3, GSK-3, IRAK-4, SYK, p70S6K, TAK-1, or ZAP-70 kinase and an equivalent sample comprising CDK-2, cMET, FLT-3, JAK-3, GSK-3, IRAK-4, SYK, p70S6K, TAK-1, or ZAP-70 kinase in the absence of said composition.

The terms "CDK-2-mediated disease" or "CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis. See Fischer, P. M. and Lane, D. P. *Current Medicinal Chemistry*, 2000, 7, 1213-1245; Mani, S., Wang, C., Wu, K., Francis, R. and Pestell, R. *Exp. Opin. Invest. Drugs* 2000, 9, 1849; Fry, D. W. and Garrett, M. D. *Current Opinion in Oncologic, Endocrine & Metabolic Investigational Drugs* 2000, 2, 40-59.

The terms "FLT-3-mediated disease" or "FLT-3-mediated condition", as used herein, mean any disease or other deleterious condition in which FLT-3 is known to play a role. The terms "FLT-3-mediated disease" or "FLT-3-mediated condition" also mean those diseases or conditions that are alleviated by treatment with a FLT-3 inhibitor. Such conditions include, without limitation, hematopoietic disorders, in particular, acute-myelogenous leukemia (AML), acute-promyelocytic leukemia (APL), and acute lymphocytic leukemia (ALL).

The term "GSK-3-mediated disease" as used herein, means any disease or other deleterious condition or disease in which GSK-3 is known to play a role. The terms "GSK-3-mediated disease" or "GSK-3-mediated condition" also mean those diseases or conditions that are alleviated by treatment with a GSK-3 inhibitor. Such diseases or conditions include, without limitation, autoimmune diseases, inflammatory diseases, metabolic, neurological and neurodegenerative diseases, cardiovascular diseases, allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia, stroke, and baldness.

The term "IRAK-4-mediated disease" as used herein, means any disease or other deleterious condition or disease in which IRAK-4 is known to play a role. The terms "IRAK-4-mediated disease" or "IRAK-4-mediated condition" also mean those diseases or conditions that are alleviated by treatment with an IRAK-4 inhibitor. Such diseases or conditions include, without limitation, autoimmune diseases, inflammatory diseases, rheumatoid arthritis, inflammatory bowel disease, sepsis, viral diseases, and cancer.

The term "JAK-3-mediated disease", as used herein means any disease or other deleterious condition in which a JAK-3 kinase, is known to play a role. The terms "JAK-3-mediated disease" or "JAK-3-mediated condition" also mean those diseases or conditions that are alleviated by treatment with an JAK-3 inhibitor. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

The term "cMET-mediated disease" or "cMET-mediated condition", as used herein, means any disease state or other deleterious condition in which cMET is known to play a role. The terms "cMET-mediated disease" or "cMET-mediated condition" also mean those diseases or conditions that are alleviated by treatment with a cMET inhibitor. Such conditions include, without limitation, renal, colon, breast, prostate, and lung cancer, atherosclerosis and lung fibrosis.

The term "p70S6K-mediated condition" or "disease", as used herein, means any disease or other deleterious condition in which p70S6K is known to play a role. The term "p70S6K-mediated condition" or "disease" also means those diseases or conditions that are alleviated by treatment with a p70S6K inhibitor. p70S6K-mediated diseases or conditions include, but are not limited to, proliferative disorders, such as cancer and tuberous sclerosis.

The term "SYK-mediated disease" or "SYK-mediated condition", as used herein, means any disease or other deleterious condition in which SYK protein kinase is known to play a role. The terms "SYK-mediated disease" or "SYK-mediated condition" also mean those diseases or conditions that are alleviated by treatment with a SYK inhibitor. Such conditions include, without limitation, allergic disorders, especially asthma.

The term "TAK-1-mediated condition", as used herein means any disease or other deleterious condition in which TAK-1 is known to play a role. The terms "TAK-1-mediated disease" or "TAK-1-mediated condition" also mean those diseases or conditions that are alleviated by treatment with an TAK inhibitor. Such conditions include, without limitation, autoimmune, inflammatory, proliferative, and hyperproliferative diseases, rheumatoid arthiritis, heart failure, osteoporosis, hepatic cancer, neurite outgrowth, adipogenesis, and cardiomyocyte differentiation.

The term "ZAP-70-mediated condition", as used herein means any disease or other deleterious condition in which ZAP-70 is known to play a role. The terms "ZAP-70-mediated disease" or "ZAP-70-mediated condition" also mean those diseases or conditions that are alleviated by treatment with a ZAP-70 inhibitor. Such conditions include, without limitation, autoimmune, inflammatory, proliferative, and hyperproliferative diseases and immunologically-mediated diseases including rejection of transplanted organs or tissues and Acquired Immunodeficiency Syndrome (AIDS).

For example, ZAP-70-mediated conditions include diseases of the respiratory tract including, without limitation, reversible obstructive airways diseases including asthma, such as bronchial, allergic, intrinsic, extrinsic and dust asthma, particularly chronic or inveterate asthma (e.g. late asthma airways hyper-responsiveness) and bronchitis. Additionally, ZAP-70 diseases include, without limitation, those conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

ZAP-70-mediated conditions also include diseases of the bone and joints including, without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

ZAP-70-mediated conditions also include diseases and disorders of the skin, including, without limitation, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, areata and vernal conjunctivitis.

ZAP-70-mediated conditions also include diseases and disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema.

ZAP-70-mediated conditions also include those diseases and disorders of other tissues and systemic disease, including, without limitation, multiple sclerosis, artherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

ZAP-70-mediated conditions also include allograft rejection including, without limitation, acute and chronic allograft rejection following for example transplantation of kidney, heart, liver, lung, bone marrow, skin and cornea; and chronic graft versus host disease.

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still another embodiment, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept®, Excelon®, and memantine; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents, and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting CDK-2, cMET, FLT-3, JAK-3, GSK-3, IRAK-4, SYK, p70S6K, TAK-1, or ZAP-70 kinase activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of CDK-2, cMET, FLT-3, JAK-3, GSK-3, IRAK-4, SYK, p70S6K, TAK-1, or ZAP-70 kinase activity in a biological sample is useful for a variety of purposes that are known to one of skill in the art. Examples of such purposes include, but are not limited to, blood transfusion, organ-transplantation, biological specimen storage, and biological assays.

SYNTHETIC EXAMPLES

Examples $^1$H NMR spectra were recorded at either 400 MHz using a Bruker DPX 400 instrument or at 500 MHz using a Bruker AMX 500 instrument. Mass Spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

As used herein, the term "$R_f$(min)" refers to the HPLC retention time, in minutes, associated with the compound. HPLC methods A & B are as described below. Chemical naming for selected compounds herein was accomplished using the naming program provided by CambridgeSoft Corporations ChemDraw Ultra®, Version 7.0.1.

HPLC method A utilized to obtain the reported retention time is as follows:
  Column: YMC column, 3×150 mm
  Linear Gradient: 10% CH$_3$CN—H$_2$O to 90% CH$_3$CN—H$_2$O over 8 minutes (0.1% TFA buffer)
  Flow Rate: 1.0 ml/min
  Detection: Diode Array, 214 nm and 254 nm.

HPLC method B utilized to obtain the reported retention times is as follows:
  Column: Phenomenex C$_{18(2)}$ column, 4.6×30 mm
  Gradient: 80% H$_2$O-20% CH$_3$CN at 0 minutes, 0% H$_2$O-100% CH$_3$CN at 2.5 minutes, 0% H$_2$O-100% CH$_3$CN at 3.5 minutes.
  Flow Rate: 2.0 ml/min
  Detection: Diode Array, 214 nm and 254 nm.

Example 1

2-(4-Methoxy-phenyl)-8-methyl-chromen-4-one oxime (I-23)

Compound I-23 was prepared according to the general method described above in Scheme 1. A stirred mixture of 8-methyl-4'-methoxyflavone (200.0 mg, 0.75 mmol), Lawesson's reagent (182.3 mg, 0.45 mmol) and anhydrous toluene (4.0 mL) was refluxed under $N_2$ for 1.5 hr. The solvent was removed under vacuum and the residue was purified by silica gel chromatography (20% ethyl acetate/hexane) to give 2-(4-Methoxy-phenyl)-8-methyl-chromene-4-thione (160.0 mg, 75.5% yield) as a red solid. Thione was used in next step without further purification. LC/MS: (M+H) 283.1. LC/Method A/8.967 min, 90.0% purity by area %.

To a solution of 2-(4-Methoxy-phenyl)-8-methyl-chromene-4-thione (160.0 mg, 0.57 mmol) in 3.5 mL of pyridine was added 118.4 mg (1.70 mmol) of hydroxylamine hydrochloride. The solution was stirred at 110° C. for 1 h. The solvent was removed under vacuum and the residue was treated with ice. The resulting slurry was filtered. The filter cake was washed with $H_2O$ and then dried overnight under vacuum to afford 137.0 mg (85.7% yield) of desired compound I-23 as a yellow solid. $^1$H NMR (500 MHz, DMSO-$d_6$) δ 10.86 (s, 1H), 7.89 (d, 2H), 7.71 (d, 1H), 7.35 (d, 1H), 7.15 (t, 1H), 7.09 (d, 2H), 7.00 (s, 1H), 3.84 (s, 3H), 2.44 (s, 3H) ppm. LC/MS: 282.1 (M+H), 280.0 (M−H), HPLC/Method A (Rt 6.268 min, 95.4% purity).

Example 2

2-(4-Methoxy-phenyl)-7-(3-morpholin-4-yl-propoxy)-chromen-4-one oxime (I-26)

Compound I-26 was prepared according to the general method described above in Scheme 3. A mixture of 7-hydroxy-4'-methoxyflavone (300.0 mg, 1.12 mmol), 1-bromo-3-chloropropane (176.3 mg, 1.12 mmol), and potassium carbonate (232.2 mg, 1.68 mol) in 8 mL of acetone was refluxed under $N_2$ for overnight. The solvent was removed under vacuum and the residue was stirred with 20 mL of methylene chloride. After filtration, the filtrate was washed with 0.5 N of NaOH (10 mL), water (2×10 mL), and brine (10 mL). The solution was dried over sodium sulfate and the solvent was removed to give a light red solid and was used in next step without further purification: yield, 367.0 mg (95.0%) of 7-(3-chloro-propoxy)-2-(4-methoxy-phenyl)-chromen-4-one. HPLC/Method A (Rt 7.933 min, 90.0% purity). MS (ES+): m/e 345.1(M+H).

A mixture of 7-(3-chloro-propoxy)-2-(4-methoxy-phenyl)-chromen-4-one (180.0 mg. 0.52 mmol), sodium iodide (156.5 mg, 1.04 mmol), potassium carbonate (173.1 mg, 1.25 mmol), and morpholine (91.0 mg, 1.04 mmol) in 5 mL of 2-butanone was refluxed under $N_2$ overnight. The solvent was removed under vacuum and the residue was stirred with EtOAc (20 mL). The solution was washed with water (2×10 mL) and brine (10 mL). After drying over sodium sulfate, the solvent was removed under vacuum to give a light yellow solid (200.0 mg, 96.9%) as 2-(4-methoxy-phenyl)-7-(3-morpholin-4-yl-propoxy)-chromen-4-one, which was used in next step without further purification. HPLC/Method A (Rt 4.40 min, 89.0% purity).

A stirred mixture of 2-(4-methoxy-phenyl)-7-(3-morpholin-4-yl-propoxy)-chromen-4-one (200.0 mg, 0.51 mmol), Lawesson's reagent (122.7 mg, 0.30 mmol) and anhydrous toluene (3.5 mL) was refluxed under $N_2$ for 1 hr. The solvent was removed under vacuum and the residue was purified by silica gel chromatography (EtOAc/MeOH/NEt$_3$, 40/2/1) to give 2-(4-methoxy-phenyl)-7-(3-morpholin-4-yl-propoxy)-chromene-4-thione (222.0 mg, 100.0% yield) as a red solid and was used in next step without further purification. MS (ES+): m/e 412.1(M+H). HPLC/Method A (Rt 5.59 min, 74.0% purity).

To a solution of 2-(4-methoxy-phenyl)-7-(3-morpholin-4-yl-propoxy)-chromene-4-thione (222.0 mg, 0.38 mmol) in 4.0 mL of pyridine was added 80.0 mg (1.15 mmol) of hydroxylamine hydrochloride. The solution was stirred at 110° C. for 2 h. The solvent was removed under vacuum and the residue was treated with ice. The resulting slurry was filtered. The filter cake was washed with $H_2O$ purified by prep HPLC to afford 71.4 mg (35.5% yield) of desired product, I-26, as a yellow syrup (TFA salt). $^1$H NMR (500 MHz, DMSO-$d_6$) δ 10.71 (s br, 1H), 9.99 (s, 1H), 7.88 (d, 2H), 7.79 (d, 1H), 7.08 (d, 2H), 7.02 (d, 1H), 6.99 (s, 1H), 6.88(dd, 1H), 4.16(t, 2H), 4.02(d, 2H), 3.84 (s, 3H), 3.67(t, 2H), 3.52(d, 2H), 3.31(t, 2H), 3.12(m, 2H), 2.17 (m, 2H) ppm. LC/MS: 411.2 (M+H), HPLC/Method A (Rt 4.03 min, 98.0% purity).

Example 3

2-(4-Methoxy-phenyl)-7-(4-morpholin-4-yl-butoxy)-chromen-4-one oxime (I-31)

Compound I-31 was prepared according to the general methods described above in Scheme 3 and for compound I-26 to give compound I-31 as a yellow solid (TFA salt, 30.1% yield, last step). $^1$H NMR (500 MHz, DMSO-$d_6$) δ10.78 (s br, 1H), 9.98(s, 1H), 7.89 (d, 2H), 7.79 (d, 1H), 7.08 (d, 2H), 7.03 (d, 1H), 7.00 (s, 1H), 6.89(dd, 1H), 4.10(t, 2H), 3.99(d, 2H), 3.84 (s, 3H), 3.67(t, 2H), 3.46(d, 2H), 3.20(m, 2H), 3.07(m, 2H), 1.81(m, 4H) ppm. LC/MS: 425.2 (M+H), 423.0 (M−H), HPLC/Method A (Rt 4.223 min, 96.2% purity).

Example 4

2-(4-Methoxy-phenyl)-7-(2-morpholin-4-yl-ethoxy)-chromen-4-one oxime (I-25)

Compound I-25 was prepared according to the general methods described above in Scheme 3 and for compound I-26 to give compound I-25 as a yellow solid (TFA salt, 47% yield, last step). $^1$H NMR (500 mHz, DMSO-$d_6$) δ10.76 (s br, 1H), 10.29 (s br, 1H), 7.89 (d, 2H), 7.81 (d, 1H), 7.11 (d, 1H), 7.08 (d, 2H), 6.99 (s, 1H), 6.95(dd, 1H), 4.47(t, 2H), 3.99(m, 2H), 3.84 (s, 3H), 3.72(m, 2H), 3.63(m, 2H), 3.54(m, 2H), 3.23(m, 2H) ppm. LC/MS: 397.2 (M+H), 395.3 (M−H); HPLC/Method A (Rt 3.93 min, 98.0% purity).

Example 5

7-Methoxy-2-[4-(4-morpholin-4-yl-butoxy)-phenyl]-chromen-4-one oxime (I-27)

Compound I-27 was prepared according to the general methods described above in Scheme 4 to give compound I-27 as a yellow syrup (TFA salt, 23% yield, last step). $^1$H NMR (500 MHz, DMSO-$d_6$) δ 10.74 (s br, 1H), 9.94 (s br, 1H), 7.90 (d, 2H), 7.78 (d, 1H), 7.07 (d, 2H), 7.01 (d, 1H), 7.00 (s, 1H), 6.89(dd, 1H), 4.10(t, 2H), 4.00(d, 2H), 3.84 (s, 3H), 3.66(t, 2H), 3.46(d, 2H), 3.20(m, 2H), 3.07(m, 2H), 1.81(m, 4H) ppm. LC/MS: 425.2 (M+H), HPLC/Method A (Rt 4.06 min, 100% purity).

Example 6

7-Methoxy-2-[4-(3-morpholin-4-yl-propoxy)-phenyl]-chromen-4-one oxime (I-28)

Compound I-28 was prepared according to the general methods described above in Scheme 4 to give compound I-28 as a yellow solid (TFA salt, 30.1% yield, last step). $^1$H-NMR (500 MHz, DMSO-$d_6$) δ10.22 (s br, 1H), 7.93 (d, 2H), 7.82 (d, 1H), 7.09 (d, 2H), 7.01 (s, 2H), 6.92(dd, 1H), 4.17(t, 2H), 4.01(d, 2H), 3.86 (s, 3H), 3.69(t, 2H), 3.52(d, 2H), 3.32(t, 2H), 3.13(m, 2H), 2.18(m, 2H) ppm. LC/MS: 411.2 (M+H), 409.0 (M−H), HPLC/Method A (Rt 3.85 min, 97.5% purity).

Example 7

7-Methoxy-2-[4-(2-morpholin-4-yl-ethoxy)-phenyl]-chromen-4-one oxime (I-29)

Compound I-29 was prepared according to the general methods described above in Scheme 4 to give compound I-29 as a yellow solid (TFA salt, 36.2% yield, last step). $^1$H NMR (500 MHz, DMSO-$d_6$) δ 10.76 (s br, 1H), 10.26(s br, 1H), 7.93 (d, 2H), 7.78 (d, 1H), 7.15 (d, 2H), 7.02 (m, 2H), 6.90(dd, 1H), 4.46(t, 2H), 4.01(m, 2H), 3.84 (s, 3H), 3.72(t, 2H), 3.62(m, 2H), 3.55(m, 2H), 3.23(m, 2H) ppm. LC/MS: 397.2 (M+H), 395.1 (M−H), HPLC/Method A (3.68 min, 100%).

Example 8

6-Fluoro-2-pyridin-3-yl-chromen-4-one oxime (I-30)

Compound I-30 was prepared according to the general method described above in Scheme 2. To a solution of 500 mg (3.25 mmol) of 5-fluoro-2-hydroxyacetophenone and 348 mg (3.25 mmol) of pyridine-3-carbaldehyde in 6 mL of ethanol was added 910 mg of 50% aqueous sodium hydroxide at 0-5° C. This was warmed up to RT and stirred at RT for 2 days. The reaction mixture was added to a mixture of 6N hydrochloric acid and ice to neutralize the base, this was filtered and washed with water to give 1-(5-fluoro-2-hydroxy-phenyl)-3-pyridin-3-yl-propenone as a yellow solid (620 mg, 78.5% yield) which was used in next step without further purification. HPLC/Method A/4.256 min, 100% purity by area %.

1-(5-Fluoro-2-hydroxy-phenyl)-3-pyridin-3-yl-propenone (256 mg, 1.05 mmol) was suspended in DMSO (2.5 mL) and a crystal of iodine added to it. The mixture was refluxed for 10 min, cooled, diluted with water and the solid obtained was filtered off then washed with 20% aqueous sodium thiosulphate to give 6-fluoro-2-pyridin-3-yl-chromen-4-one as a dark purple solid (250.0 mg, 91.5% yield) which was used in the next step without further purification. LC/Method A/3.90 min, 93.0% purity by area %. MS (FIA): m/e 242.1 (M+H).

A stirred mixture of 6-fluoro-2-pyridin-3-yl-chromen-4-one (128 mg, 0.53 mmol), Lawesson's reagent (129 mg, 0.32 mmol) and anhydrous toluene (3.5 mL) was refluxed under $N_2$ for 0.5 hr. The solvent was removed under vacuum and the residue was purified by silica gel chromatography (EtOAc/MeOH/NEt$_3$, 40/2/1) to give 6-fluoro-2-pyridin-3-yl-chromene-4-thione (114.0 mg, 83.6% yield) as a brown yellow solid which was used in next step without further purification. LC/MS: 258.1 (M+H); LC/Method A/5.94 min, 96.6% purity by area %.

To a solution of 6-fluoro-2-pyridin-3-yl-chromene-4-thione (114 mg, 0.44 mmol) in 3.0 mL of pyridine was added 92 mg (1.33 mmol) of hydroxylamine hydrochloride. The solution was stirred at 110° C. for 15 min. The solvent was removed under vacuum and the residue was treated with ice. The resulting slurry was filtered. The filter cake was washed with H$_2$O and purified by prep HPLC to afford 40.0 mg (24.6% yield) of compound, I-30, as a bright yellow solid (TFA salt). $^1$H NMR (500 MHz, DMSO-$d_6$) δ 11.34 (s, 1H), 9.22(s, 1H), 8.75 (d, 1H), 8.48 (d, 1H), 7.67 (m, 1H), 7.55 (m, 2H), 7.41 (m, 1H), 7.26(s, 1H) ppm. LC/MS: 257.1 (M+H); LC/Method A/3.82 min, 98.0% purity by area %.

Example 9

2-(4-Methoxy-phenyl)-6-methyl-chromen-4-one oxime (I-32)

Compound I-32 was prepared according to the general method described above in Scheme 1 to give compound I-32 as a yellow solid (31.7% yield, last step). $^1$H NMR (500 MHz, DMSO-$d_6$) δ 10.83 (s, 1H), 7.87 (d, 2H), 7.67 (s, 1H), 7.31 (s, 2H), 7.06 (d, 2H), 6.98 (s, 1H), 3.83 (s, 3H), 2.34(s, 3H) ppm. LC/MS: 282.1(M+H); LC/Method A/6.29 min, 100% purity by area %.

Table 2 below depicts Mass Spec, HPLC, and $^1$H-NMR data for certain compounds of the invention:

TABLE 2

| Compound | M.Spec. (M + H)+ | HPLC, $R_t$(min). Method A or B | $^1$H-NMR |
|---|---|---|---|
| I-11 | 256 | 2.07 (B) | (400MHz, DMSO-$d_6$) δ 7.1(1H, s), 7.4(1H, m), 7.6(5H, m), 8.0(2H, m), 11.2(1H, s) ppm. |
| I-12 | 286 | 2.13 (B) | (400MHz, DMSO-$d_6$) δ 3.85(3H, s), 7.0(1H, s), 7.1(2H, d), 7.4(1H, m), 7.6(2H, m), 7.9 (2H, m), 11.1(1H, s) ppm. |
| I-13 | 298 | 2.05 (B) | (400MHz, DMSO-$d_6$) δ 3.9(6H, 2s), 6.9(1H, s), 7.1(3H, m), 7.6(3H, m), 7.8(1H, d), 10.8 (1H, s) ppm. |
| I-14 | 272 | 2.05 (B) | (400MHz, DMSO-$d_6$) δ 6.8(1H, s), 7.3(2H, m), 7.5-7.8(5H, m), 7.9(1H, m), 11.0(1H, s) ppm. |
| I-15 | 252 | 2.13 (B) | (400MHz, DMSO-$d_6$) δ 2.4(3H, s), 7.1(1H, s), 7.2(1H, m), 7.3(1H, m), 7.5(3H, m), 7.7 (1H, d), 7.9(2H, m), 10.9(1H, s) ppm. |
| I-16 | 220 | 1.45 (B) | (400MHz, DMSO-$d_6$) δ 0.90(3H, m), 1.65 (2H, m), 2.65(2H, m), 6.40(1H, d), 6.50(1H, s), 6.55(1H, s), 7.55(1H, d), 9.90(1H, s), 10.40(1H, s) ppm. |
| I-17 | 358 | 1.61 (B) | (400MHz, DMSO-$d_6$) δ 3.8-3.9(12H, 4s), 6.75(1H, d), 7.00-7.15(3H, m), 7.4-7.6(3H, m), 9.9(1H, s), 10.8(1H, s) ppm. |

TABLE 2-continued

| Compound | M.Spec. (M + H)+ | HPLC, R$_t$(min). Method A or B | $^1$H-NMR |
|---|---|---|---|
| I-18 | 284 | 1.61 (B) | (400MHz, DMSO-d$_6$) δ 3.85(3H, s), 6.90 (3H, m), 7.15(1H, d), 7.35(2H, m), 7.80(2H, m), 10.10(1H, s), 10.80(1H, s) ppm. |
| I-19 | 298 | 1.80 (B) | (400MHz, DMSO-d$_6$) δ 3.9(6H, s), 7.0-8.0 (8H), 10.8(1H, s) ppm. |
| I-20 | 254 | 1.73 (B) | (400MHz, DMSO-d$_6$) δ 6.90(3H, m), 7.30 (1H, d), 7.40(1H, d), 7.50(1H, m), 7.80(2H, m), 7.90(1H, d), 10.10(1H, br s), 10.80(1H, s) ppm. |
| I-21 | 335 | 1.99 (B) | (400MHz, DMSO-d$_6$) δ 1.7(2H, m), 1.8(2H, m), 2.6(2H, m), 4.1(2H, m), 6.9-7.1(3H), 7.5(3H, m), 7.8(1H, d), 8.0(2H, m), 10.8 (1H, s) ppm. |
| I-23 | 280 | 6.27 (A) | (500MHz, DMSO-d$_6$) δ 10.86(s, 1H), 7.89 (d, 2H), 7.71(d, 1H), 7.35(d, 1H), 7.15(t, 1H), 7.09(d, 2H), 7.00(s, 1H), 3.84(s, 3H), 2.44(s, 3H) ppm. |
| I-24 | 365 | 5.74 (A) | (500MHz, DMSO-d$_6$) δ 10.75(s br, 1H), 7.90(d, 2H), 7.78(d, 2H), 7.08(d, 2H), 7.04 (d, 1H), 7.01(s, 1H), 6.89(dd, 1H), 4.10(t, 2H), 3.84(s, 3H), 2.60(t, 2H), 1.84(m, 2H), 1.74(m, 2H) ppm. |
| I-25 | 397 | 3.93 (A) | (500MHz, DMSO-d$_6$) δ 10.76(s br, 1H), 10.29(s br, 1H), 7.89(d, 2H), 7.81(d, 1H), 7.11(d, 2H), 7.08(d, 2H), 6.99(s, 1H), 6.95(dd, 1H), 4.47(t, 2H), 3.99(m, 2H), 3.84 (s, 3H), 3.72(m, 2H), 3.63(m, 2H), 3.54(m, 2H), 3.23(m, 2H) ppm. |
| I-26 | 411 | 4.03 (A) | (500MHz, DMSO-d$_6$) δ 10.71(s br, 1H), 9.99(s, 1H), 7.88(d, 2H), 7.79(d, 1H), 7.08 (d, 2H), 7.02(d, 1H), 6.99(s, 1H), 6.88(dd, 1H), 4.16(t, 2H), 4.02(d, 2H), 3.84(s, 3H), 3.67(t, 2H), 3.52(d, 2H), 3.31(t, 2H), 3.12(m, 2H), 2.17(m, 2H) ppm. |
| I-27 | 425 | 4.06 (A) | (500MHz, DMSO-d$_6$) δ 10.74(s br, 1H), 9.94(s br, 1H), 7.90(d, 2H), 7.78(d, 1H), 7.07(d, 2H), 7.01(d, 1H), 7.00(s, 1H), 6.89(dd, 1H), 4.10(t, 2H), 4.00(d, 2H), 3.84 (s, 3H), 3.66(t, 2H), 3.46(d, 2H), 3.20(m, 2H), 3.07(m, 2H), 1.81(m, 4H) ppm. |
| I-28 | 411 | 3.85 (A) | (500MHz, DMSO-d$_6$) δ 10.22(s br, 1H), 7.93(d, 2H), 7.82(d, 1H), 7.09(d, 2H), 7.01 (s, 2H), 6.92(dd, 1H), 4.17(t, 2H), 4.01(d, 2H), 3.86(s, 3H), 3.69(t, 2H), 3.52(d, 2H), 3.32(t, 2H), 3.13(m, 2H), 2.18(m, 2H) ppm. |
| I-29 | 397 | 3.68 (A) | (500MHz, DMSO-d$_6$) δ 10.76(s br, 1H), 10.26(s br, 1H), 7.93(d, 2H), 7.78(d, 1H), 7.15(d, 2H), 7.02(m, 2H), 6.90(dd, 1H), 4.46(t, 2H), 4.01(m, 2H), 3.84(s, 3H), 3.72(t, 2H), 3.62(m, 2H), 3.55(m, 2H), 3.23(m, 2H) ppm. |
| I-30 | 257 | 3.82 (A) | (500MHz, DMSO-d$_6$) δ 11.34(s, 1H), 9.22(s, 1H), 8.75(d, 1H), 8.48(d, 1H), 7.67(m, 1H), 7.55(m, 2H), 7.41(m, 1H), 7.26(s, 1H) ppm. |
| I-31 | 425 | 4.22 (A) | (500MHz, DMSO-d$_6$) δ 10.78(s br, 1H), 9.98 (s, 1H), 7.89(d, 2H), 7.79(d, 1H), 7.08(d, 2H), 7.03(d, 1H), 7.00(s, 1H), 6.89(dd, 1H), 4.10(t, 2H), 3.99(d, 2H), 3.84(s, 3H), 3.67 (t, 2H), 3.46(d, 2H), 3.20(m, 2H), 3.07(m, 2H), 1.81(m, 4H) ppm. |
| I-32 | 282 | 6.29 (A) | (500MHz, DMSO-d$_6$) δ 10.83(s, 1H), 7.87 (d, 2H), 7.67(s, 1H), 7.31(s, 2H), 7.06(d, 2H), 6.98(s, 1H), 3.83(s, 3H), 2.34(s, 3H) ppm. |
| I-33 | 323 | 3.5 (A) | (500MHz, DMSO-d$_6$) δ 10.93(s, 1H), 7.96 (m, 2H), 7.68(d, 1H), 7.53(m, 3H), 7.11(m, 2H), 5.13(s, 2H), 3.91(s, 3H) ppm. |
| I-34 | 423.2 | 2.15 (A) | (500MHz, DMSO-d$_6$) δ 10.73(s, 1H), 9.19 (s, 1H), 7.90(d, 2H), 7.78(d, 1H), 7.07(d, 2H), 6.99(s, 1H), 4.09(t, 2H), 3.84(s, 3H), 3.45(d, 2H), 3.10(m, 2H), 2.86(q, 2H) ppm. |
| I-35 | 424.1 | 1.65 (A) | (500MHz, DMSO-d$_6$) δ 10.65(s, 1H), 7.88 (d, 2H), 7.77(d, 1H), 7.06(d, 2H), 6.98(s, 1H), 6.88(dd, 1H), 4.13(t, 2H), 3.84(s, 3H), 3.1(m, 10H), 2.78(s, 3H), 2.04(m, 2H) ppm. |

TABLE 2-continued

| Compound | M.Spec. (M + H)+ | HPLC, R$_t$(min). Method A or B | $^1$H-NMR |
|---|---|---|---|
| I-36 | 392.1 | 1.94 (A) | (500MHz, DMSO-d$_6$) δ 10.70(br s, 1H), 9.17(s, 1H), 7.87(d, 2H), 7.83(s, 1H), 7.78 (d, 2H), 7.71(s, 1H), 7.02(d, 2H), 6.99(m, 2H), 6.88(m, 1H), 4.41(t, 3H) ppm, 4.12(t, 2H), 3.85(s, 3H), 2.33(m, 2H) ppm. |
| I-37 | 409.2 | 2.05 (A) | (500MHz, DMSO-d$_6$) δ 10.72(br s, 1H), 9.42(s, 1H), 7.90(d, 2H), 7.79(d, 2H), 7.07 (d, 2H), 7.00(m, 2H), 6.89(dd, 1H), 4.15(t, 2H), 3.86(s, 3H), 3.51(d, 2H) ppm, 3.22(m, 2H), 2.92(q, 2H), 2.16(m, 2H), 1.83(m, 2H), 1.67(m, 3H), 1.39(m, 1H) ppm. |

Example 10

CDK-2 Inhibition Assay

Compounds were screened in the following manner for their ability to inhibit CDK-2 using a standard coupled enzyme assay (Fox et al., *Protein Sci.* 1998, 7, 2249).

To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 µM peptide (American Peptide, Sunnyvale, Calif.) was added a DMSO solution of a compound of the present invention to a final concentration of 30 µM. The resulting mixture was incubated at 30° C. for 10 min.

The reaction was initiated by the addition of 10 µl of CDK-2/Cyclin A stock solution to give a final concentration of 25 nM in the assay. The rates of reaction were obtained by monitoring absorbance at 340 nm over a 5-minute read time at 30° C. using a BioRad Ultramark plate reader (Hercules, Calif.). The K$_i$ values were determined from the rate data as a function of inhibitor concentration.

The compound numbers correspond to the compound numbers in Table 1 and were found to inhibit CDK-2. Certain compounds described herein were shown to have K$_i$s less than 1.0 micromolar (µM).

Example 11 cMET Inhibition Assay

Compounds were screened for their ability to inhibit cMet kinase activity using a standard coupled enzyme system (Fox et al., *Protein Sci.* 1998, 7, 2249). Reactions were carried out in a solution containing 100 mM HEPES (pH 7.5), 10 mM MgCl$_2$, 25 mM NaCl, 300 µM NADH, 1 mM DTT, and 1.5% DMSO. Final substrate concentrations in the assay were 200 µM ATP (Sigma Chemicals, St Louis, Mo.) and 10 µM poly-GluTyr (Sigma Chemical Company, St. Louis). Reactions were carried out at 30° C. and 80 nM cMet. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and a test compound of the present invention. The assay stock buffer solution (175 µl) was incubated in a 96 well plate with 5 µl of the test compound of the present invention at final concentrations spanning 0.006 µM to 12.5 µM at 30° C. for 10 min. Typically, a 12 point titration was conducted by preparing serial dilutions (from 10 mM compound stocks) with DMSO of the test compounds of the present invention in daughter plates. The reaction was initiated by the addition of 20 µl of ATP (final concentration 200 µM). Rates of reaction were obtained using a Molecular Devices Spectramax plate reader (Sunnyvale, Calif.) over 10 min at 30° C. The K$_i$ values were determined from the ratedata as a function of inhibitor concentration.

The compound numbers correspond to the compound numbers in Table 1 and were found to inhibit cMET. Certain compounds described herein were shown to have K$_i$s less than 1.0 micromolar (µM).

Example 12

Inhibition of GSK-3

Compounds were screened for their ability to inhibit GSK-3β (AA 1-420) activity using a standard coupled enzyme system (Fox et al., *Protein Sci.* 1998, 7, 2249). Reactions were carried out in a solution containing 100 mM HEPES (pH 7.5), 10 mM MgCl$_2$, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of interest. The assay stock buffer solution (175 µl) was incubated in a 96 well plate with 5 µl of the test compound of interest at final concentrations spanning 0.002 µM to 30 µM at 30° C. for 10 min. Typically, a 12 point titration was conducted by preparing serial dilutions (from 10 mM compound stocks) with DMSO of the test compounds in daughter plates. The reaction was initiated by the addition of 20 µl of ATP (final concentration 20 µM). Rates of reaction were obtained using a Molecular Devices Spectramax plate reader (Sunnyvale, Calif.) over 10 min at 30° C. The K$_i$ values were determined from the rate data as a function of inhibitor concentration.

Example 13

SYK Inhibition Assay

Compounds were screened for their ability to inhibit SYK using a standard coupled enzyme assay (Fox et al., *Protein Sci.* 1998, 7, 2249). Reactions were carried out in 100 mM HEPES (pH 7.5), 10 mM $MgCl_2$, 25 mM NaCl, 1 mM DTT and 1.5% DMSO. Final substrate concentrations in the assay were 200 µM ATP (Sigma chemical Co.) and 4 µM poly Gly-Tyr peptide (Sigma Chemical Co.). Assays were carried out at 30° C. and 200 nM SYK. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of SYK, DTT, and the test compound of interest of the present invention. 56 µl of the test reaction was placed in a 96 well plate followed by the addition of 1 µl of 2 mM DMSO stock containing the test compound of the present invention (final compound concentration 30 µM). The plate was pre-incubated for ~10 minutes at 30° C. and the reaction initiated by the addition of 10 µl of enzyme (final concentration 25 nM). Rates of reaction were obtained using a BioRad Ultramark plate reader (Hercules, Calif.) over a 5 minute read time at 30° C., and $K_i$ values for the compounds of the present invention were determined according to standard methods.

The compound numbers correspond to the compound numbers in Table 1 and were found to inhibit SYK. Certain compounds described herein were shown to have $K_i$s less than 1.0 micromolar (µM).

Example 14

ZAP-70 Inhibition Assay

Compounds were screened for their ability to inhibit ZAP-70 using a standard coupled enzyme assay (Fox et al., *Protein Sci.* 1998, 7, 2249). Assays were carried out in a mixture of 100 mM HEPES (pH 7.5), 10 mM $MgCl_2$, 25 mM NaCl, 2 mM DTT and 3% DMSO. Final substrate concentrations in the assay were 100 µM ATP (Sigma Chemicals) and 20 µM peptide (poly-4EY, Sigma Chemicals). Assays were carried out at 30° C. and 60 nM ZAP-70. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of ZAP-70 and the test compound of interest of the present invention. 55 µl of the stock solution was placed in a 96 well plate followed by addition of 2 µl of DMSO stock containing serial dilutions of the test compound of the present invention (typically starting from a final concentration of 15 µM). The plate was preincubated for 10 minutes at 30° C. and the reaction initiated by addition of 10 µl of enzyme (final concentration 60 nM). Initial reaction rates were determined with a Molecular Devices SpectraMax Plus plate reader over a 15 minute time course. $K_i$ data was calculated from non-linear regression analysis using the Prism software package (GraphPad Prism version 3.0a for Macintosh, GraphPad Software, San Diego Calif., USA).

The compound numbers correspond to the compound numbers in Table 1 and were found to inhibit ZAP-70. Certain compounds described herein were shown to have $K_i$s less than 1.0 micromolar (µM).

Example 15

FLT-3 Inhibition Assay

Compounds were screened for their ability to inhibit FLT-3 activity using a radiometric filter-binding assay. This assay monitors the $^{33}P$ incorporation into a substrate poly(Glu, Tyr) 4:1 (pE4Y). Reactions were carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 90 µM ATP and 0.5 mg/ml pE4Y (both from Sigma Chemicals, St Louis, Mo.). The final concentration of a compound of the present invention is generally between 0.01 and 5 µM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH 7.5), 10 mM $MgCl_2$, 25 mM NaCl, 1 mg/ml pE4Y and 180 µM ATP(containing 0.3 µCi of [γ-$^{33}P$] ATP for each reaction). Solution 2 contains 100 mM HEPES (pH 7.5), 10 mM $MgCl_2$, 25 mM NaCl, 2 mM DTT, 0.02% BSA and 3 nM FLT-3. The assay was run on a 96 well plate by mixing 50 µl each of Solution 1 and 2.5 ml of the compounds of the present invention. The reaction was initiated with Solution 2. After incubation for 20 minutes at room temperature, the reaction was stopped with 50 µl of 20% TCA containing 0.4 mM of ATP. All of the reaction volume was then transferred to a filter plate and washed with 5% TCA by a Harvester 9600 from TOMTEC (Hamden, Conn.). The amount of $^{33}P$ incorporation into pE4y was analyzed by a Packard Top Count Microplate Scintillation Counter (Meriden, Conn.). The data was fitted using Prism software to get an $IC_{50}$ or $K_i$.

The compound numbers correspond to the compound numbers in Table 1 and were found to inhibit FLT-3. Certain compounds described herein were shown to have $K_i$s less than 1.0 micromolar (µM).

Example 16

JAK-3 Inhibition Assay

Compounds of the present invention were screened for their ability to inhibit JAK activity using the method described by G. R. Brown et al., *Bioorg. Med. Chem. Lett.* 2000, 10, 575-579 in the following manner. Into Maxisorb plates, previously coated at 4° C. with Poly (Glu, Ala, Tyr) 6:3:1 then washed with phosphate buffered saline 0.05% and Tween (PBST), was added 2 µM ATP, 5 mM $MgCl_2$, and a solution of a compound of the present invention in DMSO. The reaction was started with JAK enzyme and the plates incubated for 60 minutes at 30° C. The plates were then washed with PBST, 100 µl HRP-Conjugated 4G10 antibody was added, and the plate incubated for 90 minutes at 30° C. The plate was again washed with PBST, 100 µl TMB solution was added, and the plates were incubated for another 30 minutes at 30° C. Sulfuric acid (100 µl of a 1M solution) was added to stop the reaction and the plate was read at 450 nm to obtain the optical densities for analysis to determine $IC_{50}$ values and $K_i$ values.

The compound numbers correspond to the compound numbers in Table 1 and were found to inhibit JAK-3. Certain compounds described herein were shown to have $K_i$s less than 1.0 micromolar (μM).

Example 17 p70S6K Inhibition Assay

Compounds were screened for their ability to inhibit p70S6K using a radioactive-phosphate incorporation assay at Upstate Biotechnology (Pitt and Lee, *J. Biomol. Screen.* 1996, 1, 47). Assays were carried put in a mixture of 8 mM MOPS (pH 7.0), 10 mM magnesium acetate, 0.2 mM EDTA. Final substrate concentrations in the assay were 15 μM ATP (Sigma Chemicals) and 100 μM peptide (Upstate Ltd., Dundee, UK). Assays were carried out at 30° C. and in the presence of p70S6K (5-10mU, Upstate Ltd., Dundee, UK) and [γ-$^{33}$P] ATP (Specific activity approx. 500 cpm/pmol, Amersham Pharmacia Biotech, Amersham, UK). An assay stock buffer solution was prepared containing all of the reagents listed above, with the exception of ATP, and the test compound of the present invention. 15 μl of the stock solution was placed in a 96 well plate followed by addition of 1 μl of 40 μM or 8μM DMSO stock containing the test compound of the present invention, in duplicate (final compound concentration 2 μM or 0.4 μM, respectively, final DMSO concentration 5%). The plate was preincubated for about 10 minutes at 30° C. and the reaction initiated by addition of 4 μl ATP (final concentration 15 μM).

The reaction was stopped after 10 minutes by the addition of 5 μl 3% phosphoric acid solution. A phosphocellulose 96 well plate (Millipore, Cat No. MAPHNOB50) was pretreated with 100 μl 100 mM phosphoric acid, 0.01% Tween-20 prior to the addition of the reaction mixture (20 μl). The spots were left to soak for at least 5 minutes, prior to wash steps (4×200 μl 100 mM phosphoric acid, 0.01% Tween-20). After drying, 20 μl Optiphase 'SuperMix' liquid scintillation cocktail (Perkin Elmer) was added to the well prior to scintillation counting (1450 Microbeta Liquid Scintillation Counter, Wallac).

Percentage inhibition of compounds of the present invention at 2 μM and 0.4 μM was calculated by comparing p70S6K activity with standard wells containing the assay mixture and DMSO without test compound. Compounds of the present invention showing high inhibition versus standard wells were titrated to determine $IC_{50}$ values.

The compound numbers correspond to the compound numbers in Table 1 and were found to inhibit p70S6K. Certain compounds described herein were shown to have $K_i$s less than 1.0 micromolar (μM).

Example 18

TAK-1 Inhibition Assay

Compounds were screened for their ability to inhibit TAK1A kinase activity using a radiometric filter binding assay. Reactions were carried out in a solution containing Buffer A (100 mM HEPES (pH 7.5), 10 mM MgCl$_2$), 25 mM NaCl, 2 mM DTT, and 1.5% DMSO. Final substrate concentrations in the assay were 50 μM ATP (a mixture of unlabeled ATP (Sigma Chemicals, St Louis, Mo.) and $^{33}$P-labeled ATP (PerkinElmer Life Sciences, Boston, Mass.) for a final specific activity of 50 Ci/mol), and 12 μM bovine myelin basic protein (MBP, Vertex Pharmaceuticals, Cambridge, Mass.). Reactions were carried out at ambient temperature (~20° C.) using 20 nM TAK1 A-TAB fusion protein. Under these conditions the extent of reaction is linear with time for a period of 2 hours.

A test compound of the present invention (1 μL in DMSO) was combined with ATP and Buffer A in a final volume of 47 μL in a 96 well plate. Typically, a 6 point titration was conducted by preparing serial dilutions (from 10 mM compound stocks) with DMSO of the test compounds of the present invention in daughter plates, for final concentrations spanning 0.046 μM to 3.73 μM. The reaction was initiated by the addition of 20 μl of an enzyme stock solution consisting of TAK1A-TAB fusion (described by Sugita, T. et al. in *Biochem. Biophys. Res. Comm.* 2002, 297, 1277-1281), MBP, Buffer A, NaCl, and DTT. The reaction was allowed to proceed for two hours at ambient temperature, then quenched with an equal volume of 10 mM unlabeled ATP in 10% trichloroacetic acid. A 110 μL aliquot of the quenched reaction was transferred to a Multiscreen PH filter plate (Millipore, Billerica, Mass.) and allowed to incubate at ambient temperature overnight (typically 16-20 hours). Following incubation the filter plates were washed with 3×150 μL aliquots of 5% trichloroacetic acid using a modified Biotek Elx405 plate washer. A 70 μL aliquot of Microscint 20 scintillation fluid (PerkinElmer) was added to each well, and the plate was then sealed and read on a TopCount NXT microplate scintillation counter (PerkinElmer). The $K_i$ values were determined from the rate data as a function of inhibitor concentration.

The compound numbers correspond to the compound numbers in Table 1 and were found to inhibit TAK-1. Certain compounds described herein were shown to have $K_i$s less than 1.0 micromolar (μM).

Example 19

IRAK-4 Inhibition Assay

Compounds were screened for their ability to inhibit IRAK-4 using a standard coupled enzyme assay (Fox et al., *Protein Sci.* 1998 7, 2249). Assays were carried out in a solution containing 100 mM HEPES (pH 7.5), 10 mM MgCl2, 25 mM NaCl, 2 mM DTT, and 2.5% DMSO. Final substrate concentrations in the assay were 600 μM ATP (Sigma Chemicals, St Louis, Mo.) and 300 μM custom peptide substrate (HMRSAMSGLHLVKRR (American Peptide, Sunnyvale, Calif.)). Final enzyme concentration in the assay was 30 nM IRAK-4. Final concentrations of the coupled enzyme system components were 2.5 mM phosphoenolpyruvate, 300 μM NADH, 30 μg/ml pyruvate kinase and 10 μg/ml lactate dehydrogenase. Assays were carried out at 30° C.

Two assay solutions were prepared. Solution 1 contains 100 mM HEPES (pH 7.5), 10 mM MgCl2, 28 mM NaCl, 2.8 mM phosphoenolpyruvate, 335 μM NADH, 335 μM peptide, and 670 μM ATP. Solution 2 contains 100 mM HEPES (pH 7.5), 10 mM MgCl2, 335 μg/ml pyruvate kinase, 112 μg/ml lactate dehydrogenase, 22 mM DTT, and 335 nM IRAK-4. 60 μl of the Solution 1 was placed in a 384 well plate, and the plate was preincubated for about 15 minutes at 30° C. The reaction was initiated by addition of 1 μl of solution containing 667 μM of the compound of the present invention dissolved in DMSO (final compound concentration 10 μM) and 6 μl of Solution 2. Rates of reaction were obtained by monitoring the change in absorbance at 340 nm over a 6 minute read time at 30° C. using a Molecular Devices SpectraMax Plus plate reader. Compounds showing greater than 50% inhibition were selected for further testing. These selected compounds were assayed again using serial dilutions prepared from the10mM DMSO stock vial. The concentration of these titrations typically ranged from 3 nM to 30 μM. The data was fit using Prism software to obtain an $IC_{50}$.

The compound numbers correspond to the compound numbers in Table 1 and were found to inhibit IRAK-4. Certain compounds described herein were shown to have $K_i$s less than 1.0 micromolar (μM).

-continued
I-17
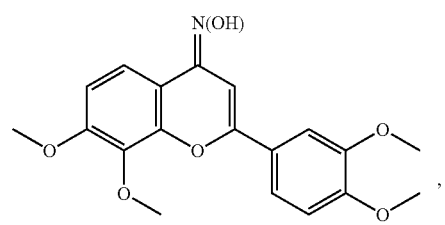
I-18
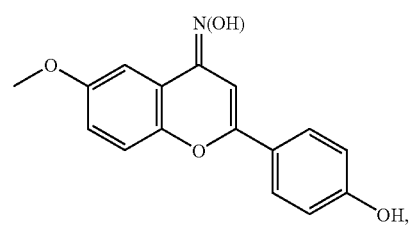
I-19
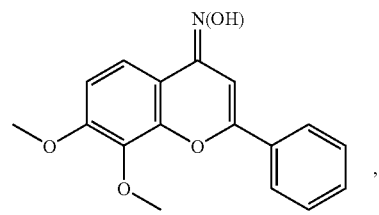
I-20
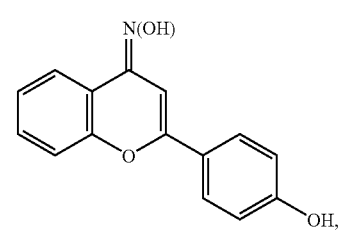
I-21
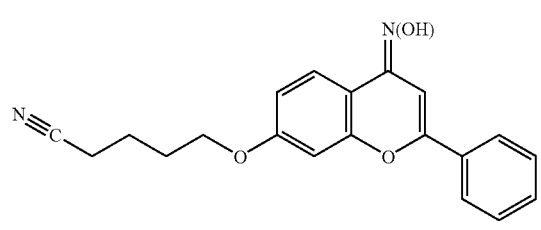
I-22
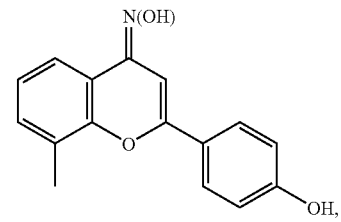
I-23
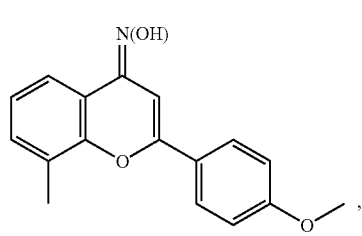
-continued
I-24
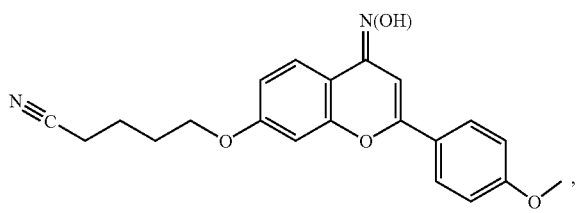
I-25
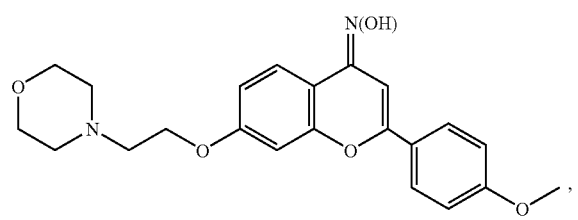
I-26
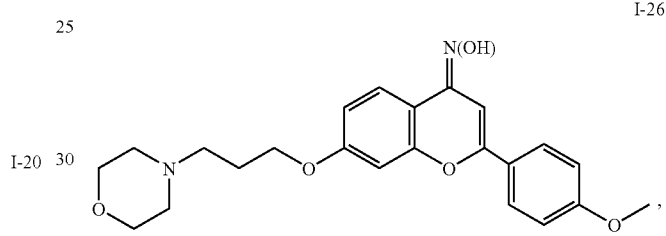
I-27
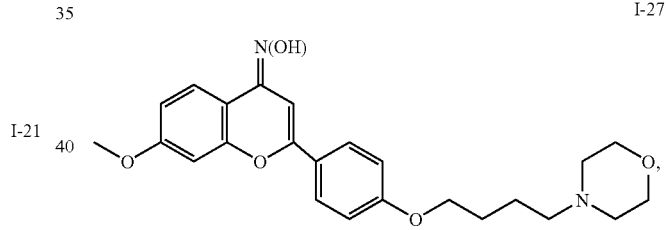
I-28
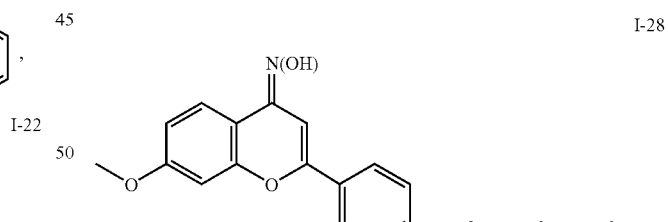
I-29
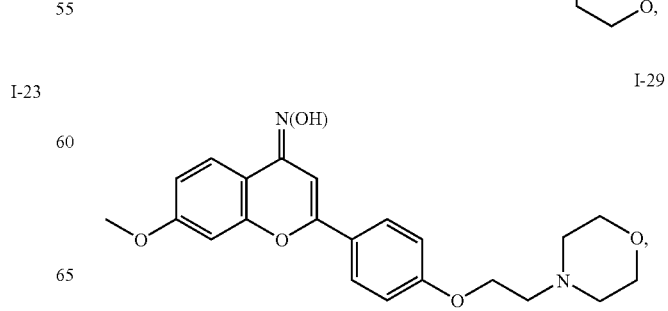

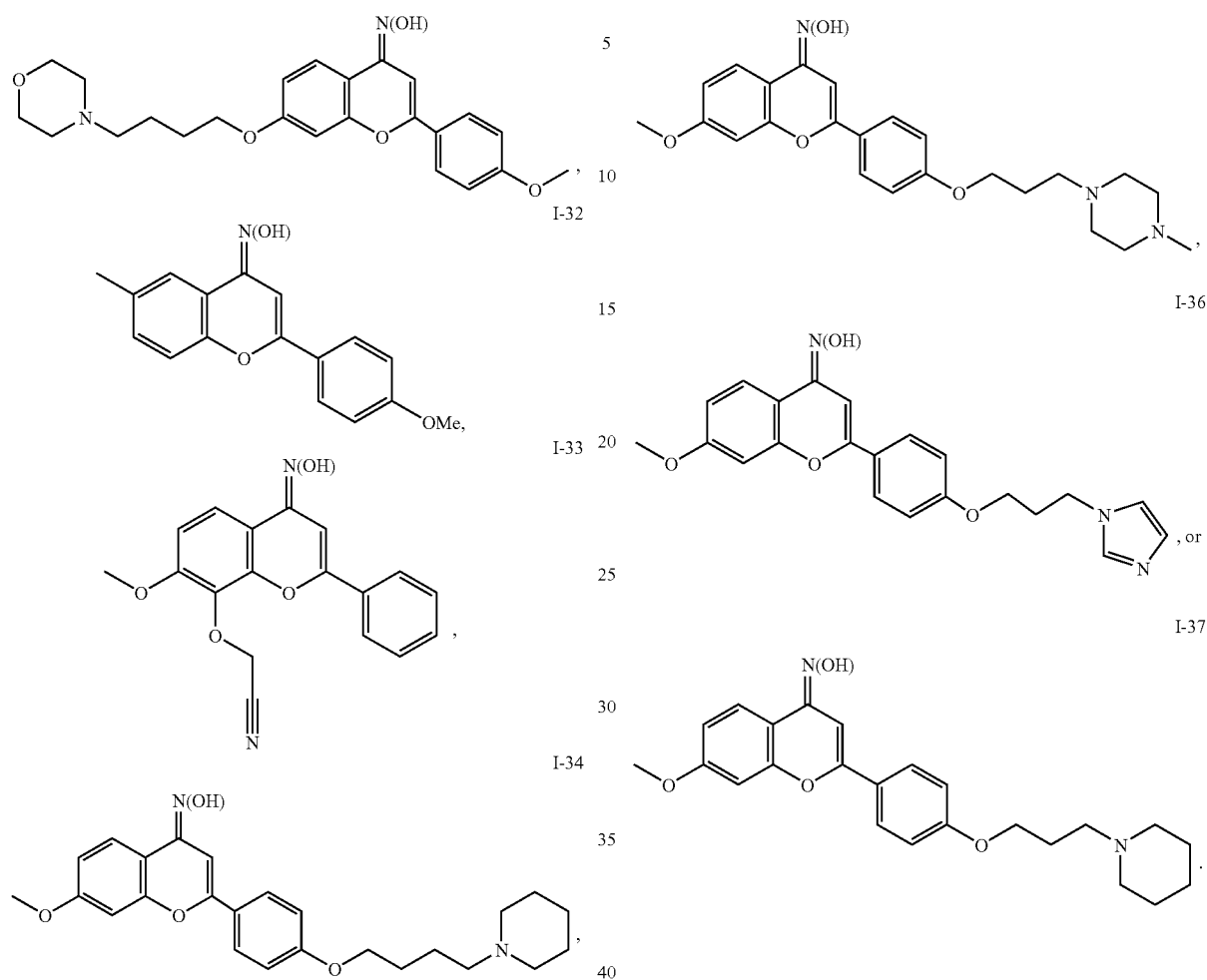

We claim:
1. A pharmaceutical composition comprising a compound of formula I:

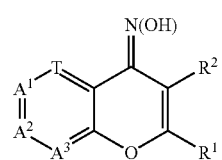

or a pharmaceutically acceptable salt thereof, and a pharmaceutically acceptable carrier, adjuvant, or vehicle, wherein:
$R^1$ is $Ar^1$;
$R^2$ is hydrogen;
T is CH;
$A^1$ is C-halogen, C—CN, or C—R;
each of $A^2$ and $A^3$ is, independently, $CR^4$;
$R^4$ is selected from halogen, $NO_2$, CN, $-(L)_mR$, $-(L)_mAr^1$, or $-(L)_mCy^1$; or
two $R^4$ groups on adjacent atoms are taken together to form an optionally substituted 5-7 membered partially unsaturated or fully unsaturated ring having 0-3 heteroatoms independently selected from oxygen, sulfur, or nitrogen, wherein each ring formed by two $R^4$ groups on adjacent atoms taken together is optionally substituted with up to 4 occurrences of Z—$R^X$;
L is a $C_{1-6}$ alkylidene chain wherein one methylene unit of L is optionally replaced by —O—, —N(R)—, —N(R)C(O)—, —C(O)—, —C(O)N(R)—, —$SO_2$N(R)—, or —N(R)$SO_2$—;
m is 0 or 1;
$Ar^1$ is

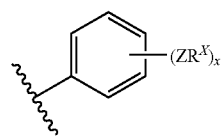

$Cy^1$ is selected from

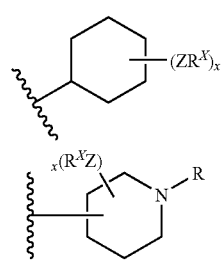

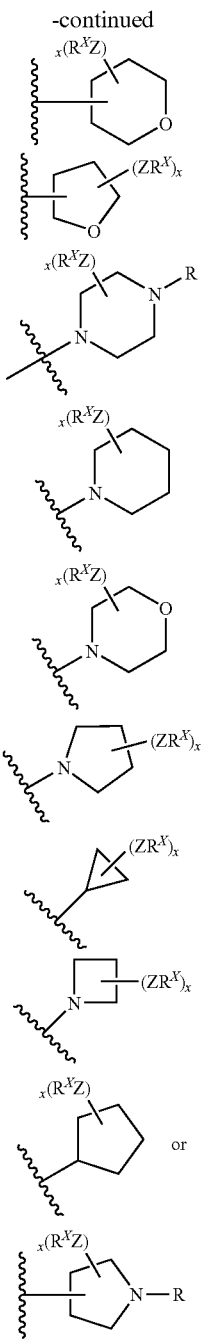

wherein;
$Ar^1$ and $Cy^1$ are each optionally substituted with up to 5 occurrences of Z-$R^X$; wherein
each occurrence of Z is independently a bond or a $C_{1-6}$ alkylidene chain, wherein up to two non-adjacent methylene units of Z are optionally replaced by —S—, —O—, —N(R)—, —N(R)C(O)—, —C(O)N(R)—, —$SO_2$N(R)—, or —N(R)$SO_2$—;
each occurrence of $R^X$ is independently selected from —R', halogen, $NO_2$, CN, —OR', —SR', or —N(R')$_2$,
each occurrence of R is independently hydrogen or a $C_{1-6}$ aliphatic group; and each occurrence of R' is independently hydrogen, a $C_{1-6}$ aliphatic group, a $C_{6-10}$ aryl ring, a heteroaryl ring having 5-10 ring atoms, or a heterocyclyl ring having 3-10 ring atoms; or R and R' or two occurrences of either R or R' are taken together with the atoms to which they are bound to form an optionally substituted 5-8 membered saturated, partially unsaturated, or aryl ring having 0-4 heteroatoms independently selected from nitrogen, oxygen, or sulfur; or two occurrences of either R' or R on the same nitrogen are taken together with the nitrogen atom to which they are bound to form an optionally substituted 5-8 membered saturated, partially unsaturated, or aryl ring having 1-4 heteroatoms independently selected from nitrogen, oxygen, or sulfur.

2. A method of inhibiting c-MET kinase activity in a biological sample, wherein said biological sample is selected from a cell culture, biopsied material obtained from a mammal, saliva, urine, feces, semen, or tears, or an extract thereof; which method comprises contacting said biological sample with a composition according to claim 1.

3. The composition according to claim 1, wherein $A^2$ is $CR^4$ and $R^4$ is halogen, CN, $-(L)_mR$, $-(L)_mAr^1$, or $-(L)_mCy^1$.

4. The composition according to claim 3, wherein $A^2$ is $CR^4$ and $R^4$ is halogen or R.

5. The composition according to claim 3, wherein $A^2$ is $CR^4$ and $R^4$ is $-(L)_mR$, wherein L is —O— or —N(R)—.

6. The composition according to claim 3, wherein $A^2$ is $CR^4$, $R^4$ is $-(L)_mCy^1$, m is 0 and $Cy^1$ is

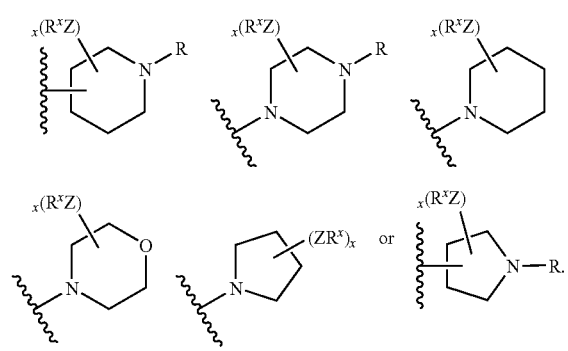

7. The composition according to claim 3, wherein $A^2$ is $CR^4$, $R^4$ is $-(L)_mR$, and compounds have the formula IE-1:

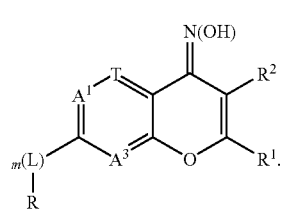

8. The composition according to claim 3, wherein $A^2$ is $CR^4$, $R^4$ is $-(L)_mAr^1$, and compounds have the formula IE-2:

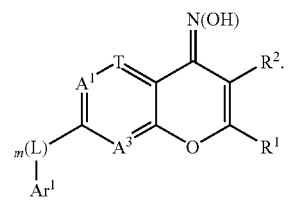

9. The composition according to claim 3, wherein $A^2$ is $CR^4$, $R^4$ is $-(L)_mCy^1$, and compounds have the formula IE-3:

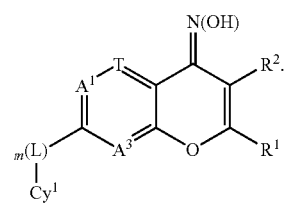

10. The composition according to claim 1, wherein $A^3$ is $CR^4$ and $R^4$ is halogen, CN, $-(L)_mR$, $-(L)_mAr^1$, or $-(L)_mCy^1$.

11. The composition according to claim 10, wherein $A^3$ is $CR^4$ and $R^4$ is halogen or R.

12. The composition according to claim 10, wherein $A^3$ is $CR^4$ and $R^4$ is $-(L)_mR$, wherein L is —O— or —N(R)—.

13. The composition according to claim 10, $A^3$ is $CR^4$, $R^4$ is $-(L)_mCy^1$, m is 0 and $Cy^1$ is

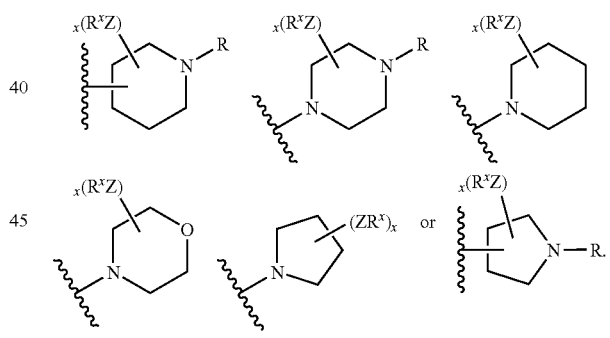

14. The composition according to claim 10, wherein $A^3$ is $CR^4$, $R^4$ is $-(L)_mR$, and compounds have the formula IF-1:

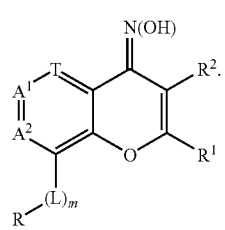

15. The composition according to claim 10, wherein $A^3$ is $CR^4$, $R^4$ is $-(L)_mAr^1$, and compounds have the formula IF-2:

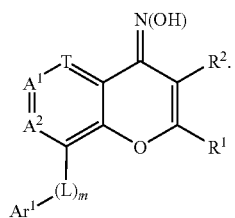
IF-2
16. The composition according to claim 10, wherein $A^3$ is $CR^4$, $R^4$ is $-(L)_m Cy^1$, and compounds have the formula IF-3:
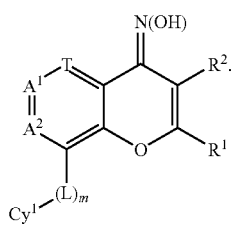
IF-3
17. The composition according to claim 1, selected from one of the following compounds:
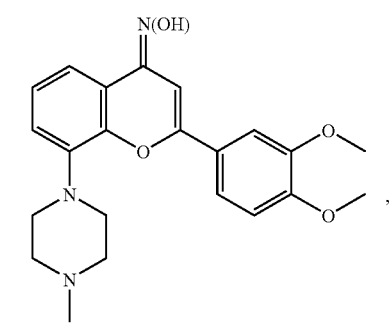
I-1
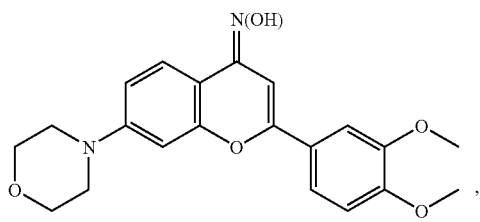
I-2
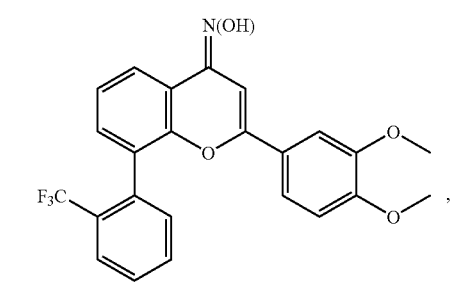
I-3
-continued
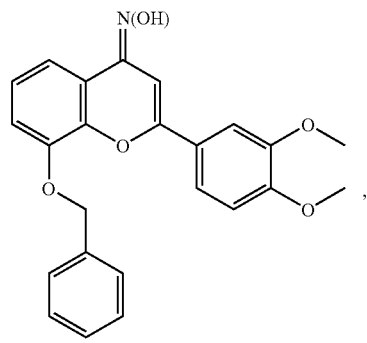
I-4
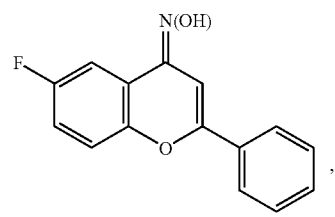
I-11
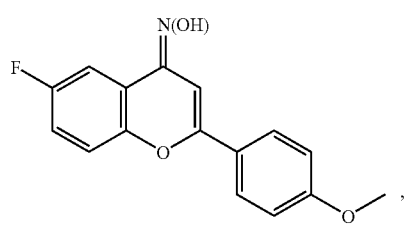
I-12
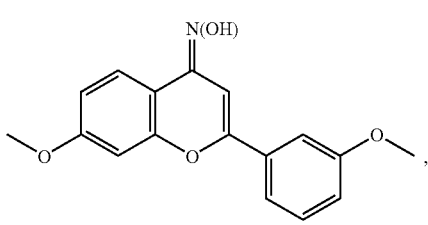
I-13
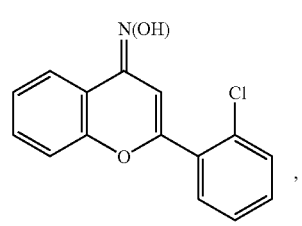
I-14
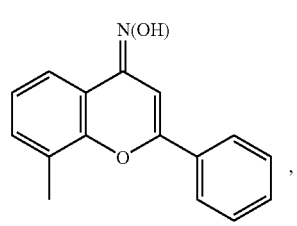
I-15